United States Patent
Natsume et al.

[11] Patent Number: 5,696,056
[45] Date of Patent: Dec. 9, 1997

[54] PHTHALIMIDE COMPOUND AND HERBICIDE CONTAINING THE SAME

[75] Inventors: Bunji Natsume; Shigeru Suzuki; Noriko Minami; Osamu Ikeda, all of Kanagawa, Japan

[73] Assignee: Mitsubishi Chemical Corporation, Tokyo, Japan

[21] Appl. No.: 789,532

[22] Filed: Jan. 27, 1997

[30] Foreign Application Priority Data

Jan. 29, 1996 [JP] Japan .................. HEI-8-012577

[51] Int. Cl.$^6$ .................. A01N 43/40; A01N 43/38; C07D 209/48; C07D 401/12
[52] U.S. Cl. .................. 504/286; 546/201; 548/476
[58] Field of Search .................. 504/286; 548/476; 546/201

[56] References Cited

U.S. PATENT DOCUMENTS

| | | | |
|---|---|---|---|
| 4,770,695 | 9/1988 | Nagano et al. | 504/286 |
| 5,405,828 | 4/1995 | Bunji et al. | 504/286 X |

FOREIGN PATENT DOCUMENTS 0 288 789  11/1988  European Pat. Off. .
0 322 401   6/1989  European Pat. Off. .

*Primary Examiner*—Michael G. Ambrose
*Attorney, Agent, or Firm*—Oblon, Spivak, McClelland, Maier & Neustadt, P.C.

[57] ABSTRACT

This invention relates to a novel phthalimide compound represented by formula:

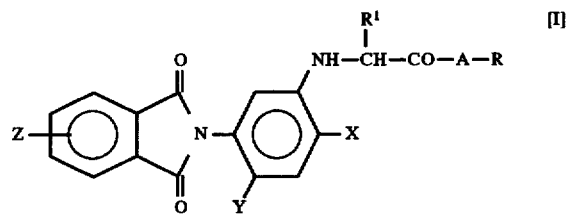

and a herbicide containing the same as an active ingredient. The compound of the present invention exhibit powerful herbicidal actions while securing sufficient safety to several important crops and are therefore useful as a herbicide.

14 Claims, No Drawings

PHTHALIMIDE COMPOUND AND HERBICIDE CONTAINING THE SAME

FIELD OF THE INVENTION

This invention relates to a novel phthalimide compound and a herbicide containing the same as an active ingredient.

BACKGROUND OF THE INVENTION

Many herbicides have been used in the cultivation of important crops, such as wheat, corn, soybeans, and rice. From the environmental consideration, herbicides have recently been required to have a high herbicidal activity at a low amount, a broad herbicidal spectrum, an appropriate residual activity, sufficient safety for crops, and the like. Under the present situation, however, none of the available herbicides satisfies these requirements sufficiently. For example, some should be used in high amounts while exhibiting broad herbicidal spectra, and some exhibit narrow herbicidal spectra while producing appreciable effect at low amounts.

On the other hand, EP-A-288789 and EP-A-384192 disclose that N-phenylphthalimide compounds having a certain substituent possess a herbicidal action.

However, the phthalimide compounds disclosed in these specifications were unsatisfactory for practical use in terms of herbicidal activity and herbicidal spectrum. An object of the present invention is to provide a phthalimide herbicide having the aforementioned properties, particularly, high controlling action at a low amount and a broad herbicidal spectrum.

SUMMARY OF THE INVENTION

As a result of extensive studies to achieve the above objects, the inventors of the present invention found that phthalimide compound having a specific substituent exhibits a high herbicidal activity and also sufficient safety for several important crops and thus completed the present invention.

Thus, the present invention relates to a phthalimide compound represented by formula (I):

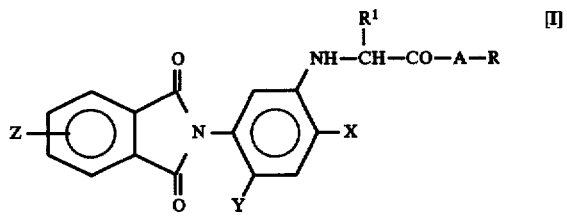

wherein A represents an oxygen atom, a sulfur atom or —NR²—, wherein R² represents a hydrogen atom or an alkyl group having 1 to 4 carbon atoms, R represents a hydrogen atom; an alkyl group having 1 to 6 carbon atoms; an alkenyl group having 2 to 6 carbon atoms; an alkynyl group having 2 to 6 carbon atoms; a cycloalkyl group having 3 to 6 carbon atoms; a haloalkyl group having 1 to 4 carbon atoms; a cyanoalkyl group having 2 to 5 carbon atoms; an alkoxyalkyl group having 2 to 6 carbon atoms; an alkylthioalkyl group having 2 to 6 carbon atoms; an alkylsulfonylalkyl group having 2 to 6 carbon atoms; an acyloxyalkyl group having 3 to 7 carbon atoms; an alkoxycarbonylalkyl group having 3 to 8 carbon atoms; a phenyl group; an alkyl group having 1 to 3 carbon atoms which is substituted with a phenyl group; a 3- to 6-membered heterocyclic group containing one or two hetero atoms selected from an oxygen atom, a sulfur atom, and a nitrogen atom; or an alkyl group having 1 to 3 carbon atoms which is substituted with a 3- to 6-membered heterocyclic group containing one or two hetero atoms selected from an oxygen atom, a sulfur atom, and a nitrogen atom, when A represents —NR²—, R may be taken together with A to form a 5- or 6-membered heterocyclic group containing one or two nitrogen atoms and zero or one oxygen atom (the heterocyclic group may be substituted with one or two methyl groups), $R^1$ represents a hydrogen atom or an alkyl group having 1 to 4 carbon atoms, X represents a halogen atom, Y represents a hydrogen atom or a halogen atom, Z represents a hydrogen atom, an alkyl group having 1 to 3 carbon atoms, or a halogen atom, and when R represents a phenyl group; an alkyl group having 1 to 3 carbon atoms which is substituted with a phenyl group; a 3- to 6-membered heterocyclic group containing one or two hetero atoms selected from an oxygen atom, a sulfur atom, and a nitrogen atom; or an alkyl group having 1 to 3 carbon atoms which is substituted with a 3- to 6-membered heterocyclic group containing one or two hetero atoms selected from an oxygen atom, a sulfur atom, and a nitrogen atom, the phenyl group or the heterocyclic group may be substituted with one to three groups, which may be the same or different and selected from a halogen atom, an alkyl group having 1 to 4 carbon atoms, a trifluoromethyl group, an alkoxy group having 1 to 4 carbon atoms, an acyloxy group having 2 to 5 carbon atoms, an alkylthio group having 1 to 4 carbon atoms, an alkylsulfonyl group having 1 to 4 carbon atoms, a nitro group, a cyano group, and an alkoxycarbonyl group having 2 to 5 carbon atoms, and also relates a herbicide comprising the above-mentioned phthalimide compound as an active ingredient.

DETAILED DESCRIPTION OF THE INVENTION

1. Phthalimide Compound

The phthalimide compound which can be used as a herbicide in the invention is a compound represented by formula (I).

In formula (I), A is an oxygen atom, a sulfur atom or —NR²— (wherein R² represents a hydrogen atom; or an alkyl group having 1 to 4 carbon atoms, e.g., methyl, ethyl, propyl, isopropyl, butyl, isobutyl, sec-butyl or t-butyl), and A is preferably an oxygen atom or —NR²—, still preferably an oxygen atom.

R represents a hydrogen atom; an alkyl group having 1 to 6 carbon atoms (e.g., methyl, ethyl, propyl, isopropyl, butyl, isobutyl, sec-butyl, t-butyl, pentyl, isopentyl, neopentyl, t-pentyl, 1-methylbutyl, 2-methylbutyl, 1-ethylpropyl, 1,2-dimethylpropyl, 1,3-dimethylpropyl, hexyl, isohexyl, 1-methylpentyl, 2-methylpentyl, 3-methylpentyl, 1,1-dimethylbutyl, 1,2-dimethylbutyl, 1,3-dimethylbutyl, 3,3-dimethylbutyl, 1-ethylbutyl, 2-ethylbutyl, 1,1,2-trimethylpropyl, 1-ethyl-1-methylpropyl, 1-ethyl-2-methylpropyl); an alkenyl group having 2 to 6 carbon atoms (e.g., vinyl, allyl, 1-propenyl, isopropenyl, 1-butenyl, 2-butenyl, 3-butenyl, 1-methylallyl, 2-methylallyl, 1-pentenyl, 2-pentenyl, 3-pentenyl, 4-pentenyl, 1-methyl-2-butenyl, 1-methyl-3-butenyl, 2-methyl-3-butenyl, 3-methyl-2-butenyl, 3-methyl-3-butenyl, 1,1-dimethylallyl, 1-ethylallyl, 1-hexenyl, 2-hexenyl, 3-hexenyl, 4-hexenyl, 5-hexenyl, 4-methyl-3-pentenyl, 1-propylallyl, 1-ethyl-1-methylallyl); an alkynyl group having 2 to 6 carbon atoms (e.g., ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-3-butynyl, 1,1-dimethyl-2-propynyl, 1-hexynyl, 2-hexynyl, 3-hexynyl, 4-hexynyl, 5-hexynyl); a cycloalkyl group having 3 to 6 carbon atoms (e.g., cyclopropyl, cyclobutyl, cyclopentyl, cyclohexyl); a haloalkyl group having 1 to 4 carbon atoms (e.g., fluoromethyl, chloromethyl, bromomethyl, difluoromethyl, trifluoromethyl, 2-fluoroethyl, 2-chloroethyl, 2-bromoethyl, 2,2,2-trifluoroethyl, 3-fluoropropyl, 3-chloropropyl, 3-bromopropyl, 2,2,3,3,3-pentafluoropropyl, 2,2,2-trifluoro-1-methylethyl, 4-fluorobutyl, 4-chlorobutyl, 4-bromobutyl, 2,2,3,3,4,4-heptafluorobutyl); a cyanoalkyl group having 2 to 5 carbon atoms (e.g., cyanomethyl, 1-cyanoethyl, 2-cyanoethyl, 1-cyanopropyl, 3-cyanopropyl, 1-cyanobutyl, 4-cyanobutyl); an alkoxyalkyl group having 2 to 6 carbon atoms (e.g., methoxymethyl, ethoxymethyl, propoxymethyl, isopropoxymethyl, butoxymethyl, 2-methoxyethyl, 2-ethoxyethyl, 2-propoxyethyl, 2-isopropoxyethyl, 2-butoxyethyl, 3-methoxypropyl, 4-methoxybutyl, 5-methoxypentyl); an alkylthioalkyl group having 2 to 6 carbon atoms (e.g., methylthiomethyl, ethylthiomethyl, propylthiomethyl, isopropylthiomethyl, butylthiomethyl, 2-(methylthio)ethyl, 2-(ethylthio)ethyl, 2-(propylthio)ethyl, 2-(isopropylthio)ethyl, 2-(butylthio)ethyl, 3-(methylthio)propyl, 4-(methylthio)butyl, 5-(methylthio)pentyl); an alkylsulfonylalkyl group having 2 to 6 carbon atoms (e.g., methylsulfonylmethyl, ethylsulfonylmethyl, propylsulfonylmethyl, isopropylsulfonylmethyl, butylsulfonylmethyl, 2-(methylsulfonyl)ethyl, 2-(ethylsulfonyl)ethyl, 2-(propylsulfonyl)ethyl, 2-(isopropylsulfonyl)ethyl, 2-(butylsulfonyl)ethyl, 3-(methylsulfonyl)propyl, 4-(methylsulfonyl)butyl, 5-(methylsulfonyl)pentyl); an acyloxyalkyl group having 3 to 7 carbon atoms (e.g., 2-(acetyloxy)ethyl, 2-(propionyloxy)ethyl, 2-(butyryloxy)ethyl, 2-(isobutyryloxy)ethyl, 2-(valeryloxy)ethyl, 2-(isovaleryloxy)ethyl, 2-(pivaloyloxy)ethyl, 2-(acryloyloxy)ethyl, 2-(propioloyloxy)ethylethyl, 2-(methacryloyloxy)ethyl, 2-(crotonoyloxy)ethyl, 3-(acetyloxy)propyl, 4-(acetyloxy)butyl, 5-(acetyloxy)pentyl); an alkoxycarbonylalkyl group having 3 to 8 carbon atoms (e.g., methoxycarbonylmethyl, ethoxycarbonylmethyl, propoxycarbonylmethyl, isopropoxycarbonylmethyl, butoxycarbonylmethyl, isobutoxycarbonylmethyl, sec-butoxycarbonylmethyl, t-butoxycarbonylmethyl, pentyloxycarbonylmethyl, isopentyloxycarbonylmethyl, hexyloxycarbonylmethyl, 2-(methoxycarbonyl)ethyl, 2-(ethoxycarbonyl)ethyl, 2-(propoxycarbonyl)ethyl, 2-(isopropoxycarbonyl)ethyl, 2-(butoxycarbonyl)ethyl, 2-(isobutoxycarbonyl)ethyl, 2-(sec-butoxycarbonyl)ethyl, 2-(t-butoxycarbonyl)ethyl, 2-(pentyloxycarbonyl)ethyl, 2-(isopentyloxycarbonyl)ethyl, 1-(methoxycarbonyl)ethyl, 1-(ethoxycarbonyl)ethyl, 1-(propoxycarbonyl)ethyl, 1-(isopropoxycarbonyl)ethyl, 1-(butoxycarbonyl)ethyl, 1-(isobutoxycarbonyl)ethyl, 1-(sec-butoxycarbonyl)ethyl, 1-(t-butoxycarbonyl)ethyl, 1-(pentyloxycarbonyl)ethyl, 1-(isopentyloxycarbonyl)ethyl, 3-(methoxycarbonyl)propyl, 3-(ethoxycarbonyl)propyl, 3-(propoxycarbonyl)propyl, 3-(isopropoxycarbonyl)propyl, 3-(butoxycarbonyl)propyl, 1-(methoxycarbonyl)propyl, 1-(ethoxycarbonyl)propyl, 1-(propoxycabonyl)propyl, 1-(isopropoxycarbonyl)propyl, 1-(butoxycarbonyl)propyl, 1-(methoxycarbonyl)-1-methylethyl, 1-(ethoxycarbonyl)-1-methylethyl, 1-methyl-1-(propoxycarbonyl)ethyl, 1-(isopropoxycarbonyl)-1-methylethyl, 1-(butoxycarbonyl)-1-methylethyl, 4-(methoxycarbonyl)butyl, 4-(ethoxycarbonyl)butyl, 4-(propoxycarbonyl)butyl, 3-(isopropoxycarbonyl)butyl); a phenyl group; an alkyl group having 1 to 3 carbon atoms (e.g., methyl, ethyl, propyl, isopropyl) which is substituted with a phenyl group; a 3- to 6-membered heterocyclic group containing one or two hetero atoms selected from an oxygen atom, a sulfur atom, and a nitrogen atom; or an alkyl group having 1 to 3 carbon atoms (e.g., methyl, ethyl, propyl, isopropyl) which is substituted with a 3- to 6-membered heterocyclic group containing one or two hetero atoms selected from an oxygen atom, a sulfur atom, and a nitrogen atom. When A represents —NR²—, R may be taken together with A to form a 5- or 6-membered heterocyclic ring containing one or two nitrogen atoms and zero or one oxygen atom which may be substituted with one or two methyl groups. The 3- to 6-membered heterocyclic group containing one or two of an oxygen atom, a sulfur atom and a nitrogen atom includes an oxiranyl group, an oxetanyl group, a tetrahydrofuryl group, a furyl group, a thienyl group, a pyrrolyl group, a pyrrolidinyl group, an oxazolyl group, a thiazolyl group, an imidazolyl group, an isooxazolyl group, an isothiazolyl group, a pyrazolyl group, a tetrahydropyranyl group, a pyridyl group, a piperidyl group, a pyrimidinyl group, a pyridazinyl group, a morpholinyl group, and a piperazinyl group. The 5- or 6-membered heterocyclic group containing one or two nitrogen atoms and zero or one oxygen atom includes a 1-pyrrolidinyl group, a 1-pyrrolyl group, a 2-isooxazolidinyl group, a 1-pyrazolyl group, a 1-imidazolyl group, a 1-piperidyl group, a 4-morpholinyl group, a perhydro-1,2-oxazin-2-yl group, and a 1-piperazinyl group.

When R represents a phenyl group; an alkyl group having 1 to 3 carbon atoms which is substituted with a phenyl group; a 3- to 6-membered heterocyclic group containing one or two hetero atoms selected from an oxygen atom, a sulfur atom, and a nitrogen atom; or an alkyl group having 1 to 3 carbon atoms which is substituted with a 3- to 6-membered heterocyclic group containing one or two hetero atoms selected from an oxygen atom, a sulfur atom, and a nitrogen atom, the phenyl group or the heterocyclic group may be substituted with one to three groups, which may be the same or different, selected from a halogen atom (e.g., fluorine, chlorine, bromine, iodine); an alkyl group having 1 to 4 carbon atoms (e.g., methyl, ethyl, propyl, isopropyl, butyl, isobutyl, sec-butyl, t-butyl); a trifluoromethyl group; an alkoxy group having 1 to 4 carbon atoms (e.g., methoxy, ethoxy, propoxy, isopropoxy, butoxy, isobutyoxy, sec-butoxy, t-butoxy); an acyloxy group having 2 to 5 carbon atoms (e.g., acetyloxy, propionyloxy, butyryloxy, isobutyryloxy, valeryloxy, isovaleryloxy, pivaloyloxy, acryloyloxy, propioloyloxy, methacryloyloxy, crotonoyloxy); an alkylthio group having 1 to 4 carbon atoms (e.g., methylthio, ethylthio, propylthio, isopropylthio, butylthio, isobutylthio, sec-butylthio, t-butylthio); an alkylsulfonyl group having 1 to 4 carbon atoms (e.g., methylsulfonyl, ethylsulfonyl, propylsulfonyl, isopropylsulfonyl, butylsulfonyl, isobutylsulfonyl, sec-butylsulfonyl, t-butylsulfonyl); a nitro group; a cyano group; and an alkoxycarbonyl group having 2 to 5 carbon atoms (e.g., methoxycarbonyl, ethoxycarbonyl, propoxycarbonyl, isopropoxycarbonyl, butoxycarbonyl, isobutoxycarbonyl, sec-butoxycarbonyl t-butoxycarbonyl).

R preferably represents a hydrogen atom; an alkyl group having 1 to 6 carbon atoms; an alkenyl group having 2 to 6 carbon atoms; an alkynyl group having 2 to 6 carbon atom; a cycloalkyl group having 3 to 6 carbon atoms; a haloalkyl group having 1 to 4 carbon atoms; a cyanoalkyl group having 2 to 5 carbon atoms; an alkoxyalkyl group having 2 to 6 carbon atoms; an acyloxyalkyl group having 3 to 7 carbon atoms; an alkoxycarbonylalkyl group having 3 to 8 carbon atoms; a phenyl group; an alkyl group having 1 to 3 carbon atoms which is substituted with a phenyl group; a tetrahydrofuryl group substituted with an acyloxy group having 2 to 5 carbon atoms; or a tetrahydropyran-2-ylmethyl group. When A represents —$NR^2$—, it is also preferable that R is taken together with A to form a piperidino group. R still preferably represents a hydrogen atom; an alkyl group having 1 to 6 carbon atoms; an alkenyl group having 2 to 6 carbon atoms; an alkynyl group having 2 to 6 carbon atoms; a cycloalkyl group having 3 to 6 carbon atoms; a haloalkyl group having 1 to 4 carbon atoms; a cyanoalkyl group having 2 to 5 carbon atoms; an alkoxyalkyl group having 2 to 6 carbon atoms; an acyloxyalkyl group having 3 to 7 carbon atoms; an alkoxycarbonylalkyl group having 3 to 8 carbon atoms; an alkyl group having 1 to 3 carbon atoms which is substituted with a phenyl group; a tetrahydrofuryl group substituted with an acyloxy group having 2 to 5 carbon atoms; or a tetrahydropyran-2-ylmethyl group.

$R^1$ represents a hydrogen atom; or an alkyl group having 1 to 4 carbon atoms (e.g., methyl, ethyl, propyl, isopropyl, butyl, isobutyl, sec-butyl, t-butyl), preferably a hydrogen atom or an alkyl group having 1 to 3 carbon atoms.

X represents a halogen atom (e.g., fluorine, chlorine, bromine, iodine), preferably a chlorine atom or a bromine atom.

Y represents a hydrogen atom; or a halogen atom (e.g., fluorine, chloride, bromine, iodine), preferably a hydrogen atom, a fluorine atom or a chlorine atom.

Z represents a hydrogen atom; an alkyl group having 1 to 3 carbon atoms (e.g., methyl, ethyl, propyl, isopropyl); or a halogen atom (e.g., fluorine, chlorine, bromine, iodine), preferably a hydrogen atom, a methyl group or a halogen atom, particularly preferably a hydrogen atom, a fluorine atom or a chlorine atom. Z is preferably substituted at the 4-position.

2. Preparation of Phthalimide Compound

The process for preparing the compounds of the invention is now described. The compounds represented by formula (I) can be prepared by, for example, according to any of the following processes (1) to (4).

Process (1):

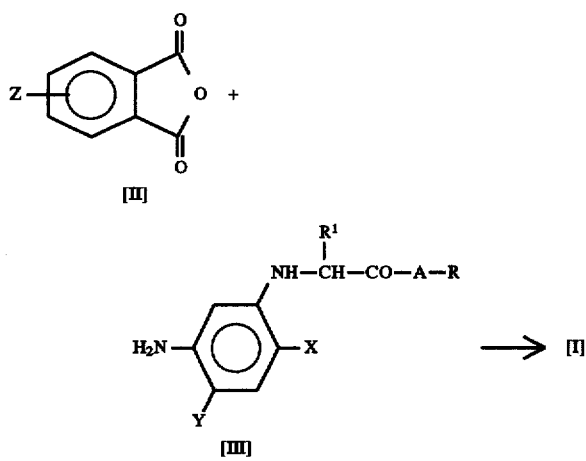

wherein A, R, $R^1$, X, Y, and Z are as defined above.

The above reaction is carried out in the presence or absence of a solvent usually at a temperature of 50° to 200° C., preferably 50° to 150° C. The compound (III) is used usually in an amount of 0.5 to 2 equivalents, preferably 0.8 to 1.2 equivalents, to 1 equivalent of the compound (II). Suitable solvents., if used, include aliphatic hydrocarbons (e.g., hexane, heptane), aromatic hydrocarbons (e.g., benzene, toluene, xylene), halogenated hydrocarbons (e.g., dichloromethane, chloroform, 1,2-dichloroethane, chlorobenzene, dichlorobenzene), ethers (diethyl ether, tetrahydrofuran, dioxane), esters (e.g., ethyl acetate, butyl acetate), ketones (e.g., acetone, methyl ethyl ketone), aprotic polar solvents (e.g., N,N-dimethylformamide, N-methylpyrrolidone, dimethyl sulfoxide, sulfolane, acetonitrile), alcohols (e.g., methanol, ethanol, 2-propanol), organic acids (e.g., formic acid, acetic acid), water, and mixtures thereof. The amount of the solvent to be used is usually up to 100 times, preferably 1 to 20 times, the weight of the compound (II).

Process (2):

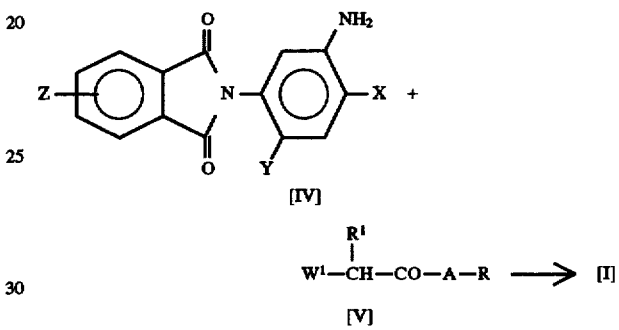

wherein A, R, $R^1$, X Y and Z are as defined above; and $W^1$ represents a halogen atom (e.g., chlorine, bromine, iodine).

The above reaction is carried out in the presence of a base with or without a solvent at a temperature usually of 50° to 200° C., preferably of 80° to 180° C. The compound (V) is used in an amount usually of from 1 to 10 equivalents, preferably of from 1 to 3 equivalents, to 1 equivalent of the compound (IV). Suitable solvents, if used, include aliphatic hydrocarbons (e.g., hexane, heptane), aromatic hydrocarbons (e.g., benzene, toluene, xylene), halogenated hydrocarbons (e.g., dichloromethane, chloroform, 1,2-dichloroethane, chlorobenzene, dichlorobenzene), ethers (diethyl ether, tetrahydrofuran, dioxane), esters (e.g., ethyl acetate, butyl acetate), ketones (e.g., acetone, methyl ethyl ketone), aprotic polar solvents (e.g., N,N-dimethylformamide, N-methylpyrrolidone, dimethyl sulfoxide, sulfolane, acetonitrile), water, and mixtures thereof. The amount of the solvent to be used is usually up to 100 times, preferably up to 10 times, the weight of the compound (IV). The base to be used includes organic bases, such as triethylamine, pyridine, picoline, N,N-diethylaniline, 4-(dimethylamino)pyridine, 1,8-diazabicyclo [5.4.0]-7-undecene, 1,5-diazabicyclo[4.3.0]-5-nonene, and 1,4-diazabicyclo[2.2.2]octane; and inorganic bases, such as sodium hydride, potassium hydride, sodium hydroxide, potassium hydroxide, sodium carbonate, potassium carbonate, sodium hydrogencarbonate, potassium hydrogencarbonate, sodium acetate, potassium acetate, sodium fluoride, and potassium fluoride. Preferred of them are sodium carbonate, potassium carbonate, sodium hydrogencarbonate, potassium hydrogencarbonate., sodium acetate, and potassium acetate. The base is used in an amount usually of 1 to 10 equivalents, preferably 1 to 3 equivalents, to 1 equivalent of the compound (IV).

Process (3):

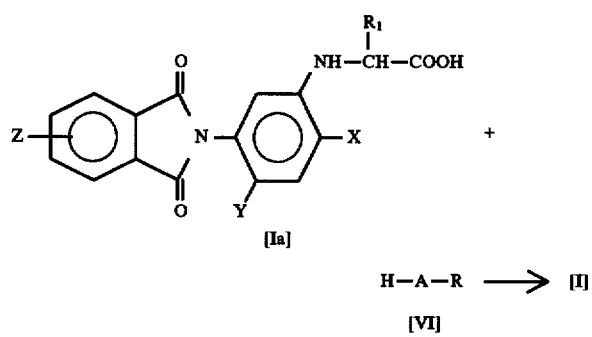

wherein A, R, R¹, X, Y, and Z are as defined above.

The conversion reaction of the carboxylic acid (Ia) and the alcohol, thiol or amine (VI) into a corresponding ester, thioester or amide (I) can be carried out according to, for example, the following methods (3-a) to (3-d).

(3-a) The compound (Ia) is converted to an acid halide by reaction with thionyl chloride, phosphorus trichloride, phosgene, etc. in the presence or absence of a base, and the resulting acid halide is then reacted with the compound (VI) in the presence or absence of a base to obtain the compound (I).

(3-b) The compound (Ia) is converted to a mixed acid anhydride by reaction with an alkyl chloroformate, trifluoroacetic anhydride, etc. in the presence or absence of a base, and the resulting mixed acid anhydride is then reacted with the compound (VI) in the presence or absence of a base to obtain the compound (I).

(3-c) The compound (Ia) is converted to an active ester by reaction with a condensing agent (e.g., dicyclohexylcarbodiimide, N,N'-carbonyldiimidazole, triphenylphosphine/carbon tetrachloride, N-alkyl-2-halogenopyridinium salts, diethyl cyanophosphonate, diphenylphosphoroazide), and the resulting ester is then reacted with the compound (VI) in the presence or absence of a base to obtain the compound (I).

(3-d) The compound (Ia) the alcohol (VI; A=O) are reacted in the presence of an acid catalyst, such as a mineral acid (e.g., hydrochloric acid, sulfuric acid), an organic acid (e.g., methanesulfonic acid, p-toluenesulfonic acid), and a Lewis acid (e.g., boron fluoride etherate) to obtain the corresponding ester (I; A=O).

The reactions of methods (3-a) to (3-d) are usually carried out in a solvent. Suitable solvents include aliphatic hydrocarbons (e.g., hexane, heptane), aromatic hydrocarbons (e.g., benzene, toluene, xylene), halogenated hydrocarbons (e.g., dichloromethane, chloroform, 1,2-dichloroethane, chlorobenzene, dichlorobenzene), ethers (diethyl ether, tetrahydrofuran, dioxane), esters (e.g., ethyl acetate, butyl acetate), ketones (e.g., acetone, methyl ethyl ketone), and aprotic polar solvents (e.g., N,N-dimethylformamide, N-methylpyrrolidone, dimethyl sulfoxide, sulfolane, acetonitrile). Suitable bases for use in the reactions (3-a) to (3-d) include those described above with respect to process (2). For the details of the reaction conditions in methods (3-a) to (3-d), refer, e.g., to *Jikken Kagaku Koza* (4th Ed.), Vol. 22, pp. 43-51, 116-121, and 144-147, edited by The Chemical Society of Japan, published by Maruzen, and reference books cited therein.

Process (4):

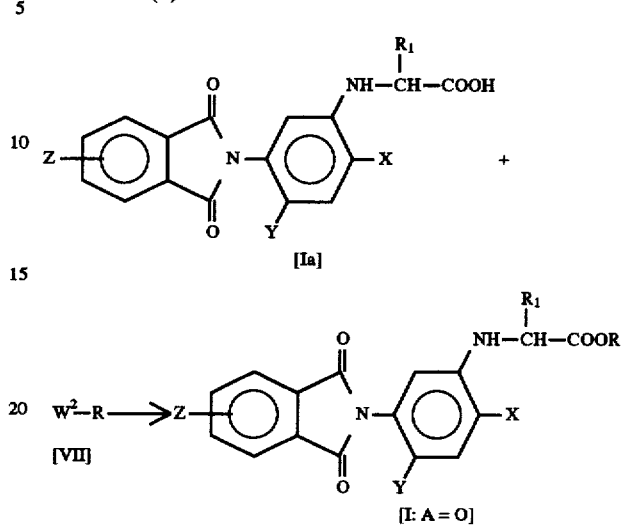

wherein R, R¹, X, Y, and Z are as defined above; and $W^2$ represents a halogen atom (e.g., chlorine, bromine, iodine).

The above reaction is carried out in the presence of a base with or without a solvent at a temperature usually of 0° to 200° C., preferably of 20° to 150° C. The compound (VII) is used in an amount usually of 1 to 10 equivalents, preferably of 1 to 3 equivalents, to 1 equivalent of the compound (Ia). Suitable solvents, if used, include aliphatic hydrocarbons (e.g., hexane, heptane), aromatic hydrocarbons (e.g., benzene, toluene, xylene), halogenated hydrocarbons (e.g., dichloromethane, chloroform, 1,2-dichloroethane, chlorobenzene, dichlorobenzene), ethers (diethyl ether, tetrahydrofuran, dioxane), esters (e.g., ethyl acetate, butyl acetate), ketones (e.g., acetone, methyl ethyl ketone), aprotic polar solvents (e.g., N,N-dimethylformamide, N-methylpyrrolidone, dimethyl sulfoxide, sulfolane, acetonitrile), water, and mixtures thereof. The amount of the solvent to be used is usually up to 200 times, preferably 1 to 20 times, the weight of the compound (Ia). The base to be used includes those described above with reference to process (2). Preferred bases are sodium hydroxide, potassium hydroxide, sodium carbonate, potassium carbonate, sodium hydrogencarbonate, potassium hydrogencarbonate, sodium acetate, potassium acetate, sodium fluoride, and potassium fluoride. The base is used in an amount usually of 1 to 10 equivalents, preferably 1 to 3 equivalents, to 1 equivalent of the compound (Ia).

The aniline compound (III) used as a starting compound in process (1) can be prepared according to the following reaction formulae (1) to (4):

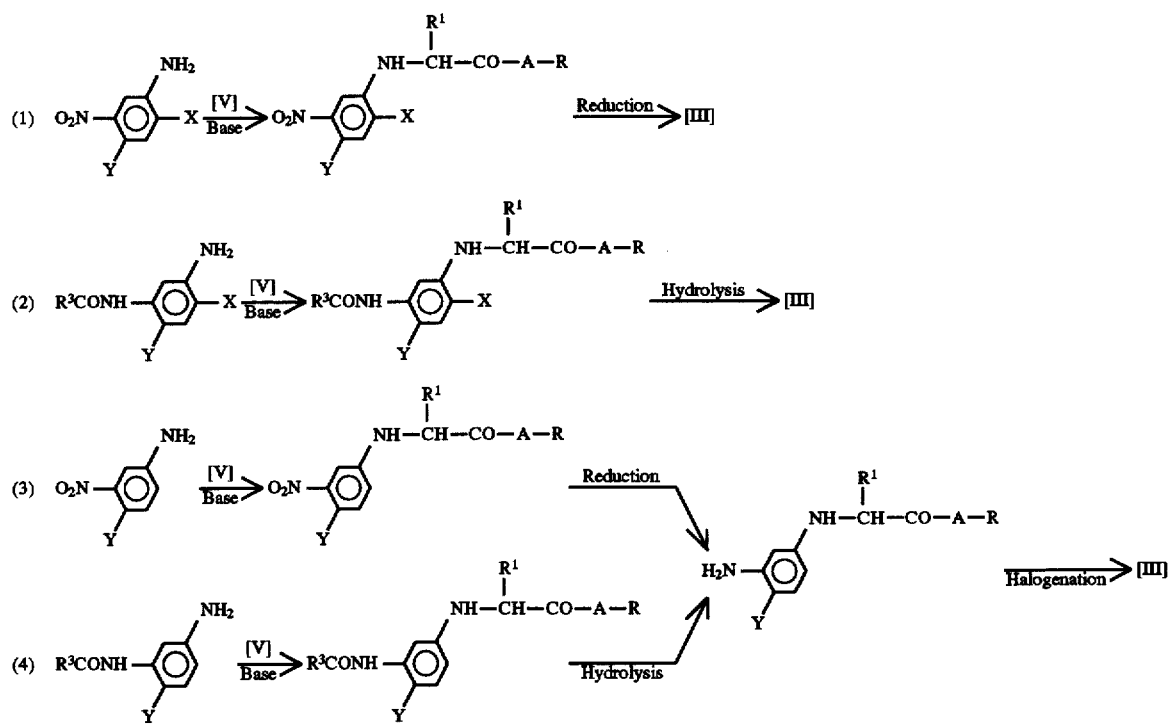

wherein A, R, R¹, X, and Y are as defined above; and R³ represents a lower alkyl group (e.g., methyl, ethyl, propyl, isopropyl).

The base used in the above reactions include those described in process (2). The reducing agent to be used includes a combination of a metal (e.g., iron, zinc, tin) and an acid (e.g., acetic acid, hydrochloric acid, sulfuric acid), sodium sulfide, ammonium sulfide, sodium hydrosulfide, sodium dithionite, and a combination of hydrogen and a catalyst (e.g., palladium-carbon, platinum-carbon, Raney nickel, rhodium-alumina). The halogenating agent includes chlorine, bromine, N-chlorosuccinimide, N-bromosuccinimide, and sulfuryl chloride. The hydrolysis is carried out in a mineral acid, such as hydrochloric acid or sulfuric acid.

The N-(aminophenyl)phthalimide (IV) which is the starting compound of process (2) can be obtained according to the following formula:

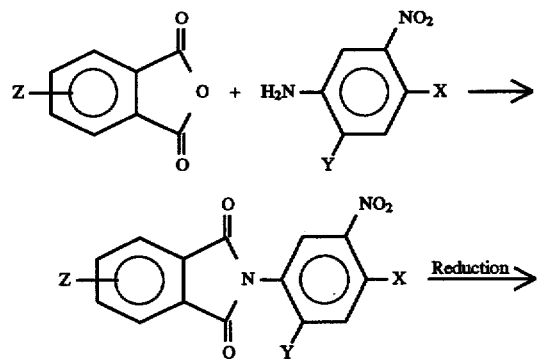

wherein X, Y, and Z are as defined above.

The imidation, the first step of the above reaction formula, is carried out under the same conditions as in process (1).

The reducing agent used in the second step includes those described with respect to the preparation of aniline compound (III).

The carboxylic acid (Ia) used as a starting compound in processes (3) and (4) is a compound of formula (I) in which —A—R is a hydroxyl group, which can be prepared by, for example, process (1).

Some of the thus obtained compounds according to the invention may occur as isomers, such as optical isomers and diastereomers, depending on their structure, all of which are included within the scope of the invention. When the compound of the invention is used as a herbicide, the amount to be applied can further be reduced by individual use of each isomer separated in a known manner. Taking into consideration the cost incurred for optical resolution, an isomeric mixture may also be used in industry.

3. Herbicide

For use as a herbicide, the compound of the invention may be applied as such but is usually formulated together with appropriate adjuvants to form wettable powders, granules, emulsifiable concentrates, flowable preparations, and the like. Useful adjuvants include solid carriers, such as kaoline, bentonite, talc, diatomaceous earth, white carbon, and starch; solvents, such as water, alcohols (e.g., methanol, ethanol, propanol, butanol, ethylene glycol), ketones (e.g., acetone, methyl ethyl ketone, cyclohexanone), ethers (e.g., diethyl ether, dioxane, cellosolve), aliphatic hydrocarbons (e.g., kerosine), aromatic hydrocarbons (e.g., benzene, toluene, xylene, solvent naphtha, methylnaphthalene), halogenated hydrocarbons (e.g., dichloroethane, carbon tetrachloride, trichlorobenzene), acid amides (e.g., dimethylformamide), esters (e.g., ethyl acetate, butyl acetate, fatty acid glycerol esters), and nitriles (e.g., acetonitrile); and surface active agents, such as nonionic surface active agents (e.g., polyoxyethylene alkyl aryl ethers, polyoxyethylene sorbitan monolaurate), cationic surface active agents (e.g., alkyldimethylbenzylammonium chlorides, alkylpyridinium chlorides), anionic surface active agents (e.g., alkylbenzenesulfonates, lignin sulfonates, higher alcohol sulfates), and amphoteric surface active agents (e.g., alkyldimethylbetaines, dodecylaminoethylglycine). These solid carriers, solvents and surface active agents may be each used either individually or as a mixture of two or more thereof according to necessity.

The amount of the compound of this invention to be applied usually ranges from 2 to 2000 g/ha, preferably 5 to 1000 g/ha, still preferably 5 to 500 g/ha, in terms of the active ingredient, while varying depending on such conditions as the structure of the compound, the weeds to be controlled, the time of treatment, the method of treatment, the properties of soil, and the like.

The weeds which can be controlled by the compounds of the invention include broad-leaved weeds growing in fields, such as *Chenopodium album*, *Chenopodium album* var. *centrorubrum*, *Polygonum longisetum*, *Polygonum persicaria*, *Amaranthus lividus*, *Amaranthus viridis*, *Stellaria media*, *Lamium amplexicaule*, *Abutilon theophrasti*, *Xanthium strumarium*, *Ipomoea purpurea*, *Datura stramonium*, *Brassica juncea*, *Galium aparine*, *Viola mandshurica*, *Matricaria matricarioides*, and *Bidens pilosa*; narrow-leaved weeds in fields, such as *Digitaria ciliaris*, *Eleusine indica*, *Echinochloa crus-galli*, *Setaria viridis*; broad-leaved weeds in paddies, such as *Rotala indica*, *Lindernia procumbens*, *Monochoria vaginalis*, *Dopatrium junceum*, *Elatine triandra*, *Alisma canaliculatum*, *Sagittaria trifolia*, and *Sagittaria pygmaea*; and narrow-leaved weeds in paddies, such as *Echinochloa oryzicola* var. *hispodula*, *Cyperus difformis*, *Scirpus juncoides*, and *Cyperus serotinus*. The compounds of the invention are effective in controlling the above weeds in either pre-emergence treatment or post-emergence treatment. Further, the compounds of the invention have small influences on the crops, such as corn, wheat, barley, rice, and soybeans, in either pre-emergence treatment or post-emergence treatment and can be used as a selective herbicide.

The herbicide comprising the compound of the invention as an active ingredient can be used in combination with other agricultural chemicals, such as insecticides, bactericides, plant growth regulators, and fertilizers, which are used in the same field. It is possible to stabilize the herbicidal effect of the compound of the invention by combining with other herbicides. In this case, the compound of the invention and other herbicide may be mixed on application or be previously formulated into a mixed preparation. Examples of the herbicides that can be suitably used in combination with the compound of the invention are shown below.

Carbamate Herbicides:
2-Chloroallyl diethyldithiocarbamate, S-2,3-dichloroallyl diisopropylthiocarbamate, S-2,2,3-trichloroallyl diisopropylthiocarbamate, S-ethyl dipropylthiocarbamate, S-ethyl diisobutylthiocarbamate, S-benzyl 1,2-dimethylpropyl(ethyl)thiocarbamate, S-4-chlorobenzyl diethylthiocarbamate, S-ethyl perhydroazepine-1-thiocarboxylate, S-isopropyl perhydroazepine-1-thiocarboxylate, S-1-methyl-1-phenylethyl piperidine-1-thiocarboxylate, O-3-t-butylphenyl 6-methoxy-2-pyridyl (methyl)thiocarbamate, 3-(3,3-dimethylureido)phenyl t-butylcarbamate, 3-(methoxycarbonylamino)phenyl 3'-methylphenylcarbamate, isopropyl 3'-chlorophenylcarbamate, and methyl (4-aminophenylsulfonyl)carbamate.

Urea Herbicides:
3-(3,4-Dichlorophenyl)-1,1-dimethylurea, 3-(3,4-dichlorophenyl)-1-methoxy-1-methylurea, 1,1-dimethyl-3-[3-(trifluoromethyl)phenyl]urea, 3-[4-(4-methoxyphenoxy)phenyl]-1,1-dimethylurea, 1-(1-methyl-1-phenylethyl)-3-p-tolylurea, 3-(4-isopropylphenyl)-1,1-dimethylurea, 3-(5-t-butylisooxazol-3-yl)-1,1-dimethylurea, 1-(5-t-butyl-1,3,4-thiadiazol-2-yl)-1,3-dimethylurea, and 1-(benzothiazol-2-yl)-1,3-dimethylurea.

Amide Herbicides:
2-Chloro-2',6'-diethyl-N-(methoxymethyl)acetanilide, N-(butoxymethyl)-2-chloro-2',6'-diethylacetanilide, 2-chloro-2', 6'-diethyl-N-(2-propoxyethyl)acetanilide, 2-chloro-N-(ethoxymethyl)-6'-ethylaceto-o-toluidide, 2-chloro-6'-ethyl-N-(2-methoxy-1-methylethyl)aceto-o-toluidide, 2-chloro-N-(3-methoxy-2-thenyl)-2',6'-dimethylacetanilide, N-(chloroacetyl)-N-(2,6-diethylphenyl)glycine ethyl ester, 2-chloro-N-(2,4-dimethyl-3-thienyl)-N-(2-methoxy-1-methylethyl) acetamide, 3',4'-dichloropropionanilide, 2',4'-difluoro-2-[3-(trifluoromethyl)phenoxy]nicotinanilide, 2-(1,3-benzothiazol-2-yloxy)-N-methylacetanilide, 2-bromo-N-(α, α-dimethylbenzyl)-3,3-dimethylbutylamide, and N-[3-(1-ethyl-1-methylpropyl)isooxazol-5-yl]-2,6-dimethoxybenzamide.

Dinitroaniline Herbicides:
2,6-Dinitro-N,N-dipropyl-4-(trifluoromethyl)aniline, N-butyl-N-ethyl-2,6-dinitro-4-(trifluoromethyl)aniline, 2,6-dinitro-$N^1,N^1$-dipropyl-4-(trifluoromethyl)-m-phenylenediamine, 4-(dipropylamino)-3,5-dinitrobenzenesulfonamide, N-sec-butyl-4-t-butyl-2,6-dinitroaniline, and N-(1-ethylpropyl)-2,6-dinitro-3,4-xylidine.

Carboxylic Acid Herbicides:
(2,4-Dichlorophenoxy)acetic acid and its derivatives, (2,4,5-trichlorophenoxy)acetic acid and its derivatives, (4-chloro-2-methylphenoxy)acetic acid and its derivatives, 2-(2,4-dichlorophenoxy)propionic acid and its derivatives, 4-(2,4-dichlorophenoxy)butyric acid and its derivatives, 2,3,6-trichlorobenzoic acid and its derivatives, 3,6-dichloro-2-methoxybenzoic acid and its derivatives, 3,7-dichloroquinoline-8-carboxylic acid, 7-chloro-3-methylquinoline-8-carboxylic acid, 3,6-dichloropyridine-2-carboxylic acid and its derivatives, 4-amino-3,5,6-trichloropyridine-2-carboxylic acid and its derivatives, (3,5,6-trichloro-2-pyridyloxy)acetic acid and its derivatives, (4-amino-3,5-dichloro-6-fluoro-2-pyridyloxy)acetic acid and its derivatives, (4-chloro-2-oxobenzothiazolin-3-yl) acetic acid and its derivatives, 2-[4-(2,4-dichlorophenoxy)phenoxy]propionic acid and its derivatives, 2-[4-[5-(trifluoromethyl)-2-pyridyloxy]phenoxy]propionic acid and its derivatives, 2-[4-[3-chloro-5-(trifluoromethyl)-2-pyridyloxy]phenoxy]propionic acid and its derivatives, 2-[4-(6-chloro-1,3-benzoxazol-2-yloxy)phenoxy]propionic acid and its derivatives, 2-[4-(6-chloroquinoxalin-2-yloxy) phenoxy]propionic acid and its derivatives, and 2-[4-(4-cyano-2-fluorophenoxy)phenoxy]propionic acid and its derivatives.

Phenolic Herbicides:
3,5-Dibromo-4-hydroxybenzonitrile and its salts, 4-hydroxy-3,5-diiodobenzonitrile and its salts, and 2-t-butyl-4,6-dinitrophenol and its salts.

Cyclohexanedione Herbicides:
Methyl 3-[1-(allyloxyimino)butyl]-4-hydroxy-6,6-dimethyl-2-oxo-3-cyclohexene-1-carboxylate and its salts, 2-[1-(ethoxyimino)butyl]-5-[2-(ethylthio)propyl]-3-hydroxy-2-cyclohexen-1-one, 2-[1-(ethoxyimino)butyl]-3-hydroxy-5-(thian-3-yl)-2-cyclohexen-1-one, 2-[1-(ethoxyimino)propyl]-3-hydroxy-5-(2,4,6-trimethylphenyl)-2-cyclohexen-1-one, 2-[1-(3-chloroallyloxyimino)propyl]-

5-[2-(ethylthio)propyl]-3-hydroxy-2-cyclohexen-1-one, and 2-[2-chloro-4-(methylsulfonyl)benzoyl]cyclohexan-1,3-dione.

Diphenyl Ether Herbicides:

4-Nitrophenyl 2,4,6-trichlorophenyl ether, 2-(2,4-dichlorophenoxy)-2-nitroanisole, 2-chloro-4-(trifluoromethyl)phenyl 3-ethoxy-4-nitrophenyl ether, methyl 5-(2,4-dichlorophenoxy)-2-nitrobenzoate, and 5-[2-chloro-4-(trifluoromethyl)phenoxy]-2-nitrobenzoic acid and its salts, ethyl O-[5-[2-chloro-4-(trifluoromethyl)phenoxy]-2-nitrobenzoyl]glycolate, ethyl O-[5-(2-chloro-4-trifluoromethylphenoxy)-2-nitrobenzoyl]-DL-lactate, 5-(2-chloro-4-trifluoromethylphenoxy)-N-(methylsulfonyl)-2-nitrobenzamide, and 2-chloro-6-nitro-3-phenoxyaniline.

Sulfonylurea Herbicides:

Ethyl 2-(4-chloro-6-methoxypyrimidin-2-ylcarbamoylsulfamoyl)benzoate, methyl 2-(4,6-dimethylpyrimidin-2-ylcarbamoylsulfamoyl)benzoate, methyl 2-[4,6-bis(difluoromethoxy)pyrimidin-2-ylcarbamoylsulfamoyl]benzoate, methyl 2-(4,6-dimethoxypyrimidin-2-ylcarbamoylsulfamoylmethyl)benzoate, 1-(2-chlorophenylsulfonyl)-3-(4-methoxy-6-methyl-1,3,5-triazin-2-yl)urea, methyl 2-(4-methoxy-6-methyl-1,3,5-triazin-2-ylcarbamoylsulfamoyl)benzoate, methyl 2-[4-methoxy-6-methyl-1,3,5-triazin-2-yl(methyl)carbamoylsulfamoyl]benzoate, 1-[2-(2-chloroethoxy)phenylsulfonyl]-3-(4-methoxy-6-methyl-1,3,5-triazin-2-yl)urea, 1-(4,6-dimethoxy-1,3,5-triazin-2-yl)-3-[2-(2-methoxyethoxy)phenylsulfonyl]urea, methyl 2-[4-ethoxy-6-(methylamino)-1,3,5-triazin-2-ylcarbamoylsulfamoyl]benzoate, methyl 3-(4-methoxy-6-methyl-1,3,5-triazin-2-ylcarbamoylsulfamoyl)thiophene-2-carboxylate, ethyl 5-(4,6-dimethoxypyrimidin-2-ylcarbamoylsulfamoyl)-1-methylpyrazole-4-carboxylate, methyl 3-chloro-5-(4,6-dimethoxypyrimidin-2-ylcarbamoylsulfamoyl)-1-methylpyrazole-4-carboxylate, 1-(4,6-dimethoxypyrimidin-2-yl)-3-[3-(trifluoromethyl)-2-pyridylsulfonyl]urea, 1-(4,6-dimethoxypyrimidin-2-yl)-3-[3-(ethylsulfonyl)-2-pyridylsulfonyl]urea, 2-(4,6-dimethoxypyrimidin-2-ylcarbamoylsulfamoyl)-N,N-dimethylnicotinamide, 1-(2-chloroimidazo[1,2-a]pyridin-3-ylsulfonyl)-3-(4,6-dimethoxypyrimidin-2-yl)urea, 1-[2-(cyclopropylcarbonyl)phenylsulfamoyl]-3-(4,6-dimethoxypyrimidin-2-yl)urea, and 1-(4-methoxy-6-methyl-1,3,5-triazin-2-yl)-3-[2-(3,3,3-trifluoropropyl)phenylsulfonyl]urea.

Bipyridinium Herbicides:

1,1'-Dimethyl-4,4'-bipyridinium dichloride and 1,1'-ethylene-2,2'-bipyridinium dibromide.

Pyrazole Herbicides:

4-(2,4-Dichlorobenzoyl)-1,3-dimethylpyrazol-5-yl toluene-4-sulfonate, 2-[4-(2,4-dichlorobenzoyl)-1,3-dimethylpyrazol-5-yloxy]acetophenone, and 2-[4-(2,4-dichloro-3-methylbenzoyl)-1,3-dimethylpyrazol-5-yloxy]-4'-methylacetophenone.

Triazine Herbicides:

6-Chloro-$N^2$,$N^4$-diethyl-1,3,5-triazine-2,4-diamine, 6-chloro-$N^2$-ethyl-$N^4$-isopropyl-1,3,5-triazine-2,4-diamine, 2-[4-chloro-6-(ethylamino)-1,3,5-triazin-2-ylamino]-2-methylpropionitrile, $N^2$,$N^4$-diethyl-6-(methylthio)-1,3,5-triazine-2,4-diamine, $N^2$-(1,2-dimethylpropyl)-$N^4$-ethyl-6-methylthio)-1,3,5-triazine-2,4-diamine, $N^2$,$N^4$-diisopropyl-6-(methylthio)-1,3,5-triazine-2,4-diamine, and 4-amino-6-t-butyl-3-(methylthio)-1,2,4-triazin-5(4H)-one.

Imidazolinone Herbicides:

Methyl 2-(4-isopropyl-4-methyl-5-oxo-2-imidazolin-2-yl)-4(5)-methylbenzoate, 2-(4-isopropyl-4-methyl-5-oxo-2-imidazolin-2-yl)pyridine-3-carboxylic acid and its salts, 2-(4-isopropyl-4-methyl-5-oxo-2-imidazolin-2-yl)quinoline-3-carboxylic acid and its salts, 5-ethyl-2-(4-isopropyl-4-methyl-5-oxo-2-imidazolin-2-yl)pyridine-3-carboxylic acid and its salts, and 2-(4-isopropyl-4-methyl-5-oxo-2-imidazolin-2-yl)- 5-(methoxymethyl)pyridine-3-carboxylic acid and its salts.

Others:

1-Methyl-3-phenyl-5-[3-(trifluoromethyl)phenyl]-4-pyridone, 3-chloro-4-(chloromethyl)-1-[3-(trifluoromethyl)phenyl]-2-pyrrolidinone, 5-(methylamino)-2-phenyl-4-[3-(trifluoromethyl)phenyl]furan-3-(2H)-one, 4-chloro-5-(methylamino)-2-[3-(trifluoromethyl)phenyl]pyrazin-3(2H)-one, N,N-diethyl-3-(2,4,6-trimethylphenylsulfonyl)-1H-1,2,4-triazole-1-carboxamide, N-[2,4-dichloro-5-[4-(dichloromethyl)-4,5-dihydro-3-methyl-5-oxo-1H-1,2,4-triazol-1-yl]phenyl]methanesulfonamide, 1-[4-chloro-3-(2,2,3,3,3-pentafluoropropoxymethyl)phenyl]-5-phenyl-1H-1,2,4-triazole-3-carboxamide, 2-(chlorobenzyl)-4,4-dimethylisooxazolidin-3-one, 5-cyclopropyl-4-[2-(methylsulfonyl)-4-(trifluoromethyl)benzoyl]isooxazole, 5-t-butyl-3-(2,4-dichloro-5-isopropoxyphenyl)-1,3,4-oxadiazol-2(3H)-one, ethyl [2-chloro-5-[4-chloro-5-(difluoromethoxy)-1-methylpyrazol-3-yl]-4-fluorophenoxy]acetate, S,S'-dimethyl 2-(difluoromethyl)-4-isobutyl-6-(trifluoromethyl)pyridine-3,5-dicarbothioate, methyl 2-(difluoromethyl)-5-(4,5-dihydro-1,3-thiazol-2-yl)-4-isobutyl-6-(trifluoromethyl)pyridine-3-carboxylate, 2-chloro-6-(4,6-dimethoxypyrimidin-2-ylthio)benzoic acid and its salts, methyl 2-(4,6-dimethoxypyrimidin-2-yloxy)-6-[1-(methoxyimino)ethyl]benzoate, 2,6-bis(4,6-dimethoxypyrimidin-2-yloxy)benzoic acid and its salts, 5-bromo-3-sec-butyl-6-methylpyrimidin-2,4(1H,3H)-dione, 3-t-butyl-5-chloro-6-methylpyrimidin-2,4(1H,3H)-dione, 3-cyclohexyl-1,5,6,7-tetrahydrocyclopentapyrimidin-2,4 (3H)-dione, isopropyl 2-chloro-5-[1,2,3,6-tetrahydro-3-methyl-2,6-dioxo-4-(trifluoromethyl)pyrimidin-1-yl]benzoate, 1-methyl-4-isopropyl-2-[(2-methylphenyl)methoxy]-7-oxabicyclo[2.2.1]heptane, N-(4-chlorophenyl)-3,4,5,6-tetrahydrophthalimide, pentyl [2-chloro-4-fluoro-5-(1,3,4,5,6,7-hexahydro-1,3-dioxo-2H-isoindol-2-yl)phenoxy]acetate, 2-[7-fluoro-3,4-dihydro-3-oxo-4-(2-propynyl)-2H-1,4-benzoxazin-6-yl]-4,5,6,7-tetrahydro-1H-isoindol-1,3(2H)-dione, N-(2,6-difluorophenyl)-5-methyl[1,2,4]triazolo[1,5-a]pyrimidine-2-sulfonamide, N-(2,6-dichloro-3-methylphenyl)-5,7-dimethoxy[1,2,4]triazolo[1,5-a]pyrimidine-2-sulfonamide, 2,3-dihydro-3,3-dimethylbenzofuran-5-yl-ethanesulfonate, 2-ethoxy-2,3-dihydro-3,3-dimethylbenzofuran-5-yl methanesulfonate, methyl [[2-chloro-4-fluoro-5-[(tetrahydro-3-oxo-1H,3H-[1,3,4]thiadiazolo[3,4-a]pyridazin-1-ylidene)amino]phenyl]thio]acetate, and 2-[2-(3-chlorophenyl)-2,3-epoxypropyl]-2-ethylindan-1,3-dione.

EXAMPLES

The present invention is now illustrated in greater detail by way of Examples, but it should be understood that the invention is not construed as being limited thereto as far as is within the scope of the invention.

EXAMPLE 1:

4-Acetoxytetrahydrofuran-3-yl 2-[(2-Chloro-4-fluoro-5-phthalimidophenyl)amino]propionate A mixture of 1.62 g of 4-acetoxytetrahydrofuran-3-yl 2-[(5-amino-2-chloro-4-fluorophenyl)amino]propionate, 0.80 g of phthalic anhydride, and 10 ml of acetic acid was heated under reflux for 3 hours while stirring. Water was added to the reaction mixture, and the semi-solid formed was collected by filtration, dissolved in ethyl acetate, washed successively with a saturated aqueous solution of sodium hydrogencarbonate and a saturated aqueous solution of sodium chloride, and dried over anhydrous magnesium sulfate. The solvent was evaporated under reduced pressure, and the residue was purified by silica gel column chromatography (ethyl acetate-hexane=2:3) to give 1.98 g of the title compound (Table 1, Compound No. 32).

EXAMPLE 2:

Isopentyl 2-[(2-Chloro-5-phthalimidophenyl)amino]propionate

A mixture of 1.64 g of N-(3-amino-4-chlorophenyl)phthalimide, 2.68 g of isopentyl 2-bromopropionate, and 0.60 g of sodium hydrogencarbonate was heated at 150° C. for 5 hours while stirring. While the reaction mixture was hot, ethyl acetate was added thereto, and the reaction mixture was washed successively with water and a saturated sodium chloride aqueous solution, and dried over anhydrous magnesium sulfate. The solvent was evaporated under reduced pressure, and the residue was purified by silica gel column chromatography (ethyl acetate-hexane=1:8) to give 1.63 g of the title compound (Table 1, Compound No. 5).

EXAMPLE 3:

2-[(2-Chloro-4-fluoro-5-phthalimidophenyl)amino]-N-methyl-N-phenylpropionamide

In 20 ml of dichloromethane were dissolved 1.45 g of 2-[(2-chloro-4-fluoro-5-phthalimodophenyl)amino]propionic acid and 0.79 g of pyridine, and the solution was cooled on an ice bath. A solution of 0.57 g of thionyl chloride in 2 ml of dichloromethane was added thereto dropwise while stirring. After the addition, the stirring was continued for an additional 30 minute period at 5° to 10° C. A solution of 0.51 g of N-methylaniline and 0.49 g of triethylamine in 5 ml of dichloromethane was added to the reaction mixture at that temperature while stirring. After the addition, the reaction mixture was warmed to room temperature and allowed to stand overnight. The reaction mixture was washed successively with water, diluted hydrochloric acid, a saturated sodium hydrogencarbonate aqueous solution, and a saturated sodium chloride aqueous solution, and dried over anhydrous magnesium sulfate. The solvent was evaporated under reduced pressure, and the residue was purified by silica gel column chromatography (ethyl acetate-hexane= 1:2) to give 1.15 g of the title compound (Table 1, Compound No. 35).

EXAMPLE 4:

Benzyl 2-[2-Chloro-4-fluoro-5-phthalimidophenyl)amino]-propionate

To a mixture of 1.45 g of 2-[(2-chloro-4-fluoro-5-phthalimidophenyl)amino]propionic acid, 0.58 g of potassium fluoride, and 20 ml of acetonitrile was added 0.82 g of benzyl bromide, and the mixture was heated under reflux for 15 hours while stirring, followed by allowing the mixture to cool. Water was added to the reaction mixture, and the mixture was extracted with ethyl acetate. The organic layer was washed with a saturated sodium hydrogencarbonate aqueous solution and then with a saturated sodium chloride aqueous solution, and dried over anhydrous magnesium sulfate. The solvent was evaporated under reduced pressure, and the residue was purified by silica gel column chromatography (ethyl acetate-hexane=1:4) to give 1.38 g of the title compound (Table 1, Compound No. 31).

Other compounds shown in Table 1 below were synthesized in the same manner as in Examples 1 to 4. The structure of all the compounds prepared was confirmed by various spectral data. The physical properties and the $^1$H-NMR spectral data of the compounds shown in Table 1 are given in Table 2 below.

TABLE 1

| Compound No. | X | Y | Z | $R^1$ | —A—R |
|---|---|---|---|---|---|
| 1 | Cl | H | H | H | —O-n-$C_6H_{13}$ |
| 2 | Cl | H | H | H | —OCHCF$_3$ (CH$_3$) |
| 3 | Cl | H | H | CH$_3$ | —OC$_2$H$_5$ |
| 4 | Cl | H | H | CH$_3$ | —O-n-C$_3$H$_7$ |
| 5 | Cl | H | H | CH$_3$ | —OCH$_2$CH$_2$CH(CH$_3$)$_2$ |
| 6 | Cl | H | H | CH$_3$ | —OCH$_2$CH=CH$_2$ |
| 7 | Cl | H | H | CH$_3$ | —O-cyclopentyl |
| 8 | Cl | H | H | CH$_3$ | —OCH$_2$CH$_2$OCCH$_3$ (=O) |
| 9 | Cl | H | H | CH$_3$ | —OCH$_2$-tetrahydropyranyl |
| 10 | Cl | H | H | CH$_3$ | dioxolane-OCCH$_3$ |
| 11 | Cl | H | H | CH$_3$ | —NH-i-C$_3$H$_7$ |
| 12 | Cl | H | H | CH$_3$ | —NH-i-C$_4$H$_9$ |
| 13 | Cl | H | H | CH$_3$ | —NH—C(CH$_3$)$_2$—phenyl |
| 14 | Cl | H | H | CH$_3$ | —N(CH$_3$)$_2$ |
| 15 | Cl | F | H | CH$_3$ | —OH |
| 16 | Cl | F | H | CH$_3$ | —OCH$_3$ |
| 17 | Cl | F | H | CH$_3$ | —OC$_2$H$_5$ |
| 18 | Cl | F | H | CH$_3$ | —O-n-C$_3$H$_7$ |
| 19 | Cl | F | H | CH$_3$ | —O-i-C$_3$H$_7$ |
| 20 | Cl | F | H | CH$_3$ | —O-n-C$_4$H$_9$ |
| 21 | Cl | F | H | CH$_3$ | —O-i-C$_4$H$_9$ |
| 22 | Cl | F | H | CH$_3$ | —O-n-C$_5$H$_{11}$ |
| 23 | Cl | F | H | CH$_3$ | —OCH$_2$CH$_2$CH(CH$_3$)$_2$ |
| 24 | Cl | F | H | CH$_3$ | —OCH$_2$CH=CH$_2$ |

TABLE 1-continued

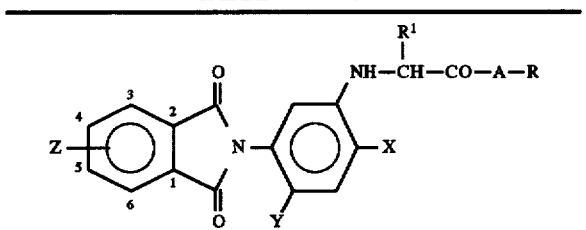

| Compound No. | X | Y | Z | R¹ | —A—R |
|---|---|---|---|---|---|
| 25 | Cl | F | H | CH₃ | —OCH₂C(CH₃)=CH₂ |
| 26 | Cl | F | H | CH₃ | —OCH₂C≡CH |
| 27 | Cl | F | H | CH₃ | —O-cyclopentyl |
| 28 | Cl | F | H | CH₃ | —OCH₂CN |
| 29 | Cl | F | H | CH₃ | —OCH₂O-n-C₃H₇ |
| 30 | Cl | F | H | CH₃ | —OCH₂COC₂H₅ |
| 31 | Cl | F | H | CH₃ | —OCH₂C₆H₅ |
| 32 | Cl | F | H | CH₃ | —O-(tetrahydrofuran-3-yl)-OCCH₃ |
| 33 | Cl | F | H | CH₃ | —NH-i-C₄H₉ |
| 34 | Cl | F | H | CH₃ | —N(CH₃)₂ |
| 35 | Cl | F | H | CH₃ | —N(CH₃)C₆H₅ |
| 36 | Cl | F | H | CH₃ | —N-piperidinyl |
| 37 | Cl | F | 3-F | CH₃ | —O-n-C₃H₇ |
| 38 | Cl | F | 3-F | CH₃ | —O-(tetrahydrofuran-3-yl)-OCCH₃ |
| 39 | Cl | F | 3-F | CH₃ | —NH-i-C₄H₉ |
| 40 | Cl | F | 4-F | CH₃ | —OH |
| 41 | Cl | F | 4-F | CH₃ | —OCH₃ |
| 42 | Cl | F | 4-F | CH₃ | —O-n-C₃H₇ |
| 43 | Cl | F | 4-F | CH₃ | —O-(tetrahydrofuran-3-yl)-OCCH₃ |
| 44 | Cl | F | 4-F | CH₃ | —NH-i-C₄H₉ |
| 45 | Cl | F | 4-Cl | CH₃ | —OH |
| 46 | Cl | F | 4-Cl | CH₃ | —OCH₃ |
| 47 | Cl | F | 4-Cl | CH₃ | —O-n-C₃H₇ |
| 48 | Cl | F | 4-CH₃ | CH₃ | —O-n-C₃H₇ |
| 49 | Cl | F | 4-CH₃ | CH₃ | —O-(tetrahydrofuran-3-yl)-OCCH₃ |
| 50 | Cl | F | 4-CH₃ | CH₃ | —NH-i-C₄H₉ |
| 51 | Cl | Cl | H | CH₃ | —OC₂H₅ |
| 52 | Cl | Cl | 4-F | CH₃ | —OC₂H₅ |
| 53 | Cl | H | H | C₂H₅ | —OC₂H₅ |
| 54 | Cl | H | H | C₂H₅ | —NH-n-C₃H₇ |
| 55 | Cl | H | H | C₂H₅ | —NH-i-C₄H₉ |
| 56 | Cl | H | H | C₂H₅ | —NH-sec-C₄H₉ |
| 57 | Cl | F | H | C₂H₅ | —NH-i-C₄H₉ |
| 58 | Cl | H | H | n-C₃H₇ | —OH |
| 59 | Cl | H | H | n-C₃H₇ | —OC₂H₅ |
| 60 | Cl | H | H | n-C₃H₇ | —O-n-C₃H₇ |
| 61 | Cl | F | H | n-C₃H₇ | —OC₂H₅ |
| 62 | Cl | F | H | n-C₃H₇ | —O-n-C₃H₇ |

TABLE 2

| Compound No | Physical Properties | 1H-NMR(δ, CDCl₃) |
|---|---|---|
| 1 | mp 100.5–101° C. | 0.88(3H, t), 1.22–1.40(6H, m), 1.58–1.70 (2H, m), 3.96(2H, d), 4.21(2H, t), 5.11 (1H, bt), 6.61(1H, d), 6.77(1H, dd), 7.39 (1H, d), 7.76–7.83(2H, m), 7.91–7.98 (2H, m) |
| 2 | mp 169.5–170° C. | 1.44(3H, d), 4.07(2H, d), 5.05(1H, bt), 5.40(1H, sep), 6.62(1H, d), 6.81(1H, dd) 7.41(1H, d), 7.76–7.83(2H, m), 7.91–7.98 (2H, m) |
| 3 | mp 123–124° C. | |
| 4 | mp 107.5–108.5° C. | |
| 5 | Viscous | 0.86(3H, d), 0.87(3H, d), 1.54(3H, d), 1.48–1.70(3H, m), 4.11–4.21(1H, m), 4.20(2H, t), 4.99(1H, bd), 6.65(1H, d), 6.76(1H, dd), 7.38(1H, d), 7.76–7.83(2H, m), 7.91–7.98(2H, m) |
| 6 | mp 132.5–133.5° C. | 1.56(3H, d), 4.15–4.25(1H, m), 4.65–4.69 (2H, m), 4.99(1H, bd), 5.20–5.34(2H, m), 5.84–5.97(1H, m), 6.66(1H, d), 6.76(1H, dd), 7.39(1H, d), 7.76–7.83(2H, m), 7.91–7.98(2H, m) |
| 7 | mp 103.5–104.5° C. | 1.51(3H, d), 1.50–1.90(8H, m), 4.08–4.18 (1H, m), 5.01(1H, bd), 5.20–5.26(1H, m), 6.65(1H, d), 6.75(1H, dd), 7.38(1H, d), |

TABLE 2-continued

| Compound No | Physical Properties | 1H-NMR(δ, CDCl₃) |
|---|---|---|
| 8 | mp 110–111° C. | 7.76–7.83(2H, m), 7.91–7.98(2H, m) 1.56(3H, d), 2.00(3H, s), 4.16–4.44(5H, m), 4.94(1H, bd), 6.67(1H, d), 6.78(1H, dd), 7.39(1H, d), 7.76–7.83(2H, m), 7.91–7.98(2H, m) |
| 9 | Glass-like | 1.18–1.60(5H, m), 1.56(3H, d), 1.74–1.87 (1H, m), 3.31–3.58(2H, m), 3.89–3.96 (1H, m)4.08–4.25(3H, m), 5.00(1H, bd), 6.65(1H, d), 6.75(1H, dd), 7.38(1H, d), 7.76–7.83(2H, m), 7.91–7.98(2H, m) |
| 10 | Glass-like | 1.57(3H, d), 1.94, 2.01(total 3H, s), 3.72–4.29(5H, m), 4.88, 4.95(total 1H, bd), 5.28–5.48(2H, m), 6.66–6.68(1H, m), 6.76–6.81(1H, m), 7.39(1H, d), 7.76–7.83 (2H, m), 7.91–7.98(2H, m) |
| 11 | mp 186.5–188° C. | |
| 12 | mp 129–130.5° C. | |
| 13 | mp 157–157.5° C. | 1.56(3H, d), 1.67(3H, s), 1.72(3H, s), 3.70–3.79(1H, m), 4.68(1H, bd), 6.64 (1H, d), 6.82(1H, bs), 6.83(1H, dd), 7.11–7.33(5H, m), 7.44(1H, m), 7.77–7.54(2H, m), 7.92–7.99(2H, m) |
| 14 | mp 204–207° C. | |
| 15 | mp 188–190° C. | 1.59(3H, d), 4.14(1H, q), 6.53(1H, d), 7.26(1H, d), 7.76–7.83(2H, m), 7.90–7.97 (2H, m) |
| 16 | mp 154.5–155° C. | 1.53(3H, d), 3.77(3H, s), 4.06–4.16(1H, m), 4.77(1H, bd), 6.50(1H, d), 7.26(1H, d), 7.77–7.84(2H, m), 7.92–7.99(2H, m) |
| 17 | mp 138.5–139.5° C. | 1.26(3H, t), 1.52(3H, d), 4.03–4.13(1H, m), 4.22(2H, q), 4.80(1H, bd), 6.51(1H, d), 7.26(1H, d), 7.77–7.84(2H, m), 7.92–7.99(2H, m) |
| 18 | mp 129.5–130.5° C. | |
| 19 | mp 105.5–106° C. | 1.21(3H, d), 1.24(3H, d), 1.50(3H, d), 4.00–4.10(1H, m), 4.82(1H, bd), 5.06(1H, sep), 6.51(1H, d), 7.25(1H, d), 7.77–7.84 (2H, m), 7.92–7.99(2H, m) |
| 20 | mp 91–91.5° C. | 0.88(3H, t), 1.26–1.38(2H, m), 1.52(3H, d), 1.54–1.64(2H, m), 4.04–4.14(1H, m), 4.16(2H, t), 4.80(1H, bd), 6.51(1H, d), 7.26(1H, d), 7.77–7.84(2H, m), 7.92–7.99 (2H, m) |
| 21 | mp 78.5–79.5° C. | 0.88(3H, d), 0.89(3H, d), 1.53(3H, d), 1.85–1.98(1H, m), 3.88–3.99(2H, m), 4.06–4.16(1H, m), 4.82(1H, bd), 6.52(1H, d), 7.26(1H, d), 7.77–7.84(2H, m), 7.92–7.99(2H, m) |
| 22 | mp 72.5–73.5° C. | 0.85(3H, t), 1.20–1.36(4H, m), 1.52(3H, d), 1.56–1.66(2H, m), 4.04–4.19(3H, m) 4.51(1H, bd), 6.51(1H, d), 7.25(1H, d), 7.77–7.84(2H, m), 7.92–7.99(2H, m) |
| 23 | mp 55–57° C. | 0.86(3H, d), 0.88(3H, d), 1.52(3H, d), 1.47–1.68(3H, m), 4.02–4.16(1H, m), 4.19(2H, t), 4.80(1H, bd), 6.51(1H, d), 7.26(1H, d), 7.77–7.84(2H, m), 7.92–7.99 (2H, m) |
| 24 | mp 150.5–151° C. | 1.54(3H, d), 4.08–4.18(1H, m), 4.64–4.67 (2H, m), 4.79(1H, bd), 5.20–5.33(2H, m), 5.82–5.96(1H, m), 6.52(1H, d), 7.26(1H, d), 7.77–7.84(2H, m), 7.92–7.99(2H, m) |
| 25 | mp 128–129° C. | 1.55(3H, d), 1.69(3H, s), 4.10–4.20(1H, m), 4.57(2H, AB), 4.81(1H, bd), 4.91(1H, s), 4.95(1H, s), 6.52(1H, d), 7.26(1H, d), 7.77–7.84(2H, m), 7.92–7.99(2H, m) |
| 26 | mp 162–163° C. | 1.56(3H, d), 2.46(3H, t), 4.10–4.20(1H, m), 4.74(1H, bd), 4.75(1H, bd), 6.51(1H, d), 7.26(1H, d), 7.77–7.84(2H, m), 7.92–7.99(2H, m) |
| 27 | mp 102.5–104° C. | 1.49(3H, d), 1.50–1.90(8H, m), 4.00–4.10 (1H, m), 4.81(1H, bd), 5.19–5.25(1H, m), 6.51(1H, d), 7.25(1H, d), 7.77–7.84(2H, m), 7.92–7.99(2H, m) |
| 28 | mp 121–122.5° C. | 1.61(3H, d), 4.15–4.25(1H, m), 4.65(1H, bd), 4.83(2H, s), 6.49(1H, d), 7.28(1H, d), 7.77–7.84(2H, m), 7.92–7.99(2H, m) |
| 29 | mp 109–110.5° C. | 0.87(3H, t), 1.56(3H, d), 1.50–1.62(2H, m), 3.45–3.57(2H, m), 4.08–4.18(1H, m), 4.79(1H, bd), 5.36(2H, AB), 6.52(1H, d), 7.26(1H, d), 7.77–7.84(2H, m), 7.92–7.99 (2H, m) |
| 30 | mp 167–167.5° C. | 1.19(3H, t), 1.62(3H, d), 4.09(2H, q), 4.16–4.26(1H, m), 4.66(2H, AB), 4.71 (1H, bd), 6.62(1H, d), 7.25(1H, d), 7.77–7.83(2H, m), 7.92–7.99(2H, m) |
| 31 | mp 145–145.5° C. | 1.53(3H, d), 4.08–4.19(1H, m), 4.78(1H, bd), 5.15(2H, AB), 6.49(1H, d), 7.20–7.32 (6H, m), 7.77–7.84(2H, m), 7.92–7.99 (2H, m) |
| 32 | Glass-like | 1.56(3H, d), 1.94–2.02(total 3H, s), 3.72–4.22(5H, m), 4.69, 4.78(total 1H, bd), 5.27–5.46(2H, m), 6.52, 6.54(total 1H, d), 7.26(1H, d), 7.77–7.84(2H, m), 7.92–7.99(2H, m) |
| 33 | mp 135–136° C. | |
| 34 | mp 209–211° C. | |
| 35 | mp 194.5–195.5° C. | 1.31(3H, d), 3.29(3H, s), 4.02–4.14(1H, m), 5.00(1H, bd), 6.11(1H, d), 7.20–7.38 (6H, m), 7.79–7.86(2H, m), 7.94–8.01 (2H, m) |
| 36 | mp 161–163.5° C. | 1.40(3H, d), 1.50–1.72(6H, m), 3.38–3.69 (4H, m), 4.30–4.40(1H, m), 5.53(1H, bd), 6.48(1H, d), 7.25(1H, d), 7.77–7.84(2H, m), 7.92–7.99(2H, m) |
| 37 | mp 140.5–141.5° C. | 0.89(3H, t), 1.53(3H, d), 1.59–1.70(2H, m), 4.04–4.18(3H, m), 4.32(1H, bd), 6.50 (1H, d), 7.26(1H, d), 7.43–7.49(1H, m), 7.76–7.84(2H, m) |
| 38 | Glass-like | 1.56(3H, d), 1.96, 2.02(total 3H, s), 3.71–4.22(5H, m), 4.69, 4.79(total 1H, bd), 5.27–5.46(2H, m), 6.51, 6.52(total 1H, d), 7.27(1H, d), 7.43–7.50(1H, m), 7.76–7.85(2H, m) |
| 39 | mp 140–141° C. | 0.84(3H, d), 0.85(3H, d), 1.58(3H, d), 1.65–1.83(1H, m), 2.98–3.17(2H, m), 3.73–3.82(1H, m), 4.48(1H, bd), 6.46 (1H, d), 6.64(1H, bt), 7.29(1H, d), 7.44–7.50(1H, m), 7.75–7.85(2H, m) |
| 40 | | 1.59(3H, d), 4.13(1H, q), 6.51(1H, d), 7.26(1H, d), 7.46(1H, ddd), 7.60(1H, d), 7.94(1H, dd) |
| 41 | mp 140–141° C. | 1.53(3H, d), 3.77(3H, s), 4.05–4.15(1H, m), 4.78(1H, bd), 6.48(1H, d), 7.26(1H, d), 7.47(1H, ddd), 7.63(1H, dd), 7.96 (1H, dd), |
| 42 | mp 76.5–77.5° C. | 0.89(3H, t), 1.53(3H, d), 1.58–1.70(2H, m), 4.05–4.18(3H, m), 4.82(1H, bd), 6.50 (1H, d), 7.26(1H, d), 7.44–7.50(1H, m), 7.63(1H, dd), 7.96(1H, dd) |
| 43 | Glass-like | 1.56(3H, d), 1.95, 2.02(total 3H, s), 3.71–4.22(5H, m), 4.69, 4.79(total 1H, bd), 5.27–5.45(2H, m), 6.50, 6.52(total 1H, d), 7.27(1H, d), 7.43–7.51(1H, m), 7.60–7.64(1H, m), 7.93–7.98(1H, m) |
| 44 | mp 101–106° C. | 0.83(3H, d), 0.84(3H, d), 1.58(3H, d), 1.65–1.83(1H, m), 2.98–3.16(2H, m), 3.73–3.82(1H, m), 4.48(1H, bd), 6.46(1H, d), 6.64(1H, bt), 7.29(1H, d), 7.44–7.50 (1H, m), 7.61(1H, dd), 7.95(1H, dd) |
| 45 | | 1.60(3H, d), 4.13(1H, q), 6.51(1H, d), 7.27(1H, d), 7.76(1H, dd), 7.88(1H, d), 7.91(1H, d) |
| 46 | mp 147.5–148° C. | 1.53(3H, d), 3.76(3H, s), 4.05–4.15(1H, m), 4.78(1H, bd), 6.48(1H, d), 7.26(1H, d), 7.76(1H, dd), 7.89(1H, d), 7.92(1H, d) |

TABLE 2-continued

| Compound No | Physical Properties | 1H-NMR(δ, CDCl₃) |
|---|---|---|
| 47 | Glass-like | 0.89(3H, t), 1.53(3H, d), 1.58–1.70(2H, m), 4.04–4.14(3H, m), 4.81(1H, bd), 6.49 (1H, d), 7.25(1H, d), 7.76(1H, dd), 7.89 (1H, d), 7.92(1H, d) |
| 48 | mp 98.5–100° C. | 0.89(3H, t), 1.52(3H, d), 1.58–1.70(2H, m), 2.55(3H, s), 4.05–4.18(3H, m), 4.80 (1H, bd), 6.51(1H, d), 7.24(1H, d), 7.58 (1H, d), 7.75(1H, s), 7.83(1H, d) |
| 49 | Glass-like | 1.55(3H, d), 1.94, 2.02(total 3H, s), 2.55 (3H, s), 3.71–4.22(5H, m), 4.68, 4.77 (total 1H, bd), 5.27–5.46(2H, m), 6.51, 6.53(total 1H, d), 7.25(1H, d), 7.59(1H, d), 7.75(1H, s), 7.83(1H, d) |
| 50 | mp 157.5–158.5° C. | 0.83(3H, d), 0.84(3H, d), 1.58(3H, d), 1.65–1.83(1H, m), 2.55(3H, s), 2.98–3.16 (2H, m)3.74–3.83(1H, m), 4.46(1H, bd), 6.47(1H, d), 6.66(1H, bt), 7.27(1H, d), 7.59(1H, d), 7.74(1H, s), 7.82(1H, d) |
| 51 | mp 145–145.5° C. | 1.25(3H, t), 1.51(3H, d), 4.04–4.14(1H, m), 4.21(2H, q), 5.00(1H, bd), 6.52(1H, s), 7.48(1H, s), 7.78–7.84(1H, m), 7.93–8.00(2H, m) |
| 52 | mp 160–160.5° C. | 1.25(3H, t), 1.52(3H, d), 4.03–4.13(1H, m), 4.21(2H, q), 5.01(1H, bd), 6.50(1H, s), 7.48(1H, s), 7.44–7.51(1H, m), 7.61–7.65(1H, m), 7.94–7.99(1H, m) |
| 53 | mp 104.5–105.5° C. | |
| 54 | mp 149–150° C. | |
| 55 | mp 123–124° C. | |
| 56 | mp 115–117° C. | |
| 57 | mp 125–126° C. | |
| 58 | mp 185.5–187° C. | |
| 59 | mp 78–79° C. | |
| 60 | ND 1.5819 (25° C.) | |
| 61 | mp 84–85° C. | |
| 62 | mp 199–101.5° C. | |

Formulation Examples of the compounds of the invention are shown below. All the parts and % are parts by weight and % by weight, respectively.

Formulation Example 1 (Wettable Powder):

Forty parts of the compound of the invention shown in Table 1, 20 parts of Carplex #80 (trade name, produced by Shionogi & Co., Ltd.), 35 parts of Kaoline Clay (trade name, produced by Tsuchiya Kaoline K.K.), and 5 parts of a higher alcohol sulfuric ester type surface active agent Solpol 8070 (trade name, produced by Toho Chemical Industry Co., Ltd.) were mixed and uniformly ground to provide a wettable powder containing 40% of the active ingredient.

Formulation Example 2 (Emulsifiable Concentrate):

Twenty parts of the compound of the invention shown in Table 1 were dissolved in a mixed solvent of 35 parts of xylene and 30 parts of N,N-dimethylformamide, and 15 parts of polyoxyethylene type surface active agent Solpol 3005X (trade name, produced by Toho Chemical Industry Co., Ltd.) was added to the solution to provide an emulsifiable concentrate containing 20% of the active ingredient.

Formulation Example 3 (Flowable):

Thirty parts of the compound of the invention shown in Table 1 were dispersed in a previously prepared mixture of 8 parts of ethylene glycol, 5 parts of Solpol AC3020 (trade name, produced by Toho Chemical Industry Co., Ltd.), 0.1 part of xantham gum, and 56.9 parts of water. The resulting slurry was wet ground in Dynomill (trade name, produced by Shinmaru Enterprises Co.) to provide a flowable containing 30% of the active ingredient.

Formulation Example 4 (Granules):

One part of the compound of the invention shown in Table 1, 43 parts of clay (produced by Nihon Talc K.K.), 55 parts of bentonite (produced by Hojun Yoko K.K.), and 1 part of a succinate type surface active agent Airrol CT-1 (trade name, produced by Toho Chemical Industry Co., Ltd.) were mixed and ground. The grinds were kneaded with 20 parts of water, and the blend was extruded from an extrusion granulator through nozzles of 0.6 mm in diameter, dried at 60° C. for 2 hours, and cut to 1 to 2 mm lengths to provide granules containing 1% of the active ingredient.

Test Examples of the compounds of the invention are shown below.

Test Example 1 (Submerged Application):

Alluvial soil from a paddy field was put in a resin-made pot having an area of 200 cm². After fertilization, an adequate amount of water was added, and the soil was paddled and leveled. Seeds of *Echinochloa oryzicola, Monochoria vaginalis, Rotala indica* or *Scirpus juncoides* were sowed within a layer 0.5 cm below the surface of the soil. Water was poured onto the soil to keep a depth of 3.5 cm.

On the 5th day from the sowing, the flowable prepared in Formulation Example 3 was diluted with water. prescribed amount of the diluted preparation was dropped to the water so as to give 10 g of the active ingredient per are (100 m²).

Cultivation was continued in a greenhouse, and the herbicidal effect was examined on the 28th day from the soil treatment. The results obtained are shown in Table 3 below (the compound numbers in Table 3 correspond to those in Table 1). The herbicidal effect was evaluated in terms of herbicidal index based on Y(%) obtained from equation:

Y=[1—(Weight of weeds above the ground in a treated pot)/(Weight of weeds above the ground in a non-treated pot)]×100 (%)

| Herbicidal Index | Y (%) |
|---|---|
| 0 | 0 to 5 |
| 1 | 6 to 30 |
| 2 | 31 to 50 |
| 3 | 51 to 70 |
| 4 | 71 to 90 |
| 5 | 91 to 100 |

TABLE 3

| Test Compound | Amount (g/ha) | Herbicidal Effect | | | |
|---|---|---|---|---|---|
| | | A | B | C | D |
| 1 | 10 | 5 | 5 | 5 | 4 |
| 2 | 10 | 4 | 5 | 4 | 3 |
| 3 | 10 | 5 | 5 | 5 | 5 |
| 4 | 10 | 5 | 5 | 5 | 5 |
| 5 | 10 | 5 | 5 | 5 | 5 |
| 6 | 10 | 5 | 5 | 5 | 5 |
| 7 | 10 | 5 | 5 | 5 | 5 |
| 8 | 10 | 4 | 5 | 5 | 3 |
| 9 | 10 | 5 | 5 | 5 | 4 |
| 10 | 10 | 5 | 5 | 4 | 3 |

TABLE 3-continued

| Test Compound | Amount (g/ha) | Herbicidal Effect | | | |
|---|---|---|---|---|---|
| | | A | B | C | D |
| 11 | 10 | 5 | 5 | 5 | 5 |
| 12 | 10 | 5 | 5 | 5 | 5 |
| 13 | 10 | 5 | 5 | 5 | 4 |
| 14 | 10 | 4 | 5 | 5 | 4 |
| 15 | 10 | 5 | 5 | 5 | 4 |
| 16 | 10 | 5 | 5 | 5 | 4 |
| 17 | 10 | 5 | 5 | 5 | 5 |
| 18 | 10 | 5 | 5 | 5 | 5 |
| 19 | 10 | 5 | 5 | 5 | 5 |
| 20 | 10 | 5 | 5 | 5 | 5 |
| 21 | 10 | 5 | 5 | 5 | 5 |
| 22 | 10 | 5 | 5 | 5 | 5 |
| 23 | 10 | 5 | 5 | 5 | 5 |
| 24 | 10 | 5 | 5 | 5 | 5 |
| 25 | 10 | 5 | 5 | 5 | 5 |
| 26 | 10 | 5 | 5 | 5 | 5 |
| 27 | 10 | 5 | 5 | 5 | 5 |
| 28 | 10 | 5 | 5 | 5 | 3 |
| 29 | 10 | 5 | 5 | 5 | 4 |
| 30 | 10 | 5 | 5 | 5 | 5 |
| 31 | 10 | 5 | 5 | 5 | 5 |
| 32 | 10 | 5 | 5 | 5 | 4 |
| 33 | 10 | 5 | 5 | 5 | 4 |
| 34 | 10 | 5 | 5 | 5 | 5 |
| 35 | 10 | 5 | 5 | 5 | 4 |
| 36 | 10 | 5 | 5 | 5 | 5 |
| 37 | 10 | 5 | 5 | 5 | 3 |
| 38 | 10 | 5 | 5 | 5 | 3 |
| 39 | 10 | 5 | 5 | 5 | 4 |
| 40 | 10 | 4 | 5 | 5 | 3 |
| 41 | 10 | 5 | 5 | 5 | 4 |
| 42 | 10 | 5 | 5 | 5 | 5 |
| 43 | 10 | 5 | 5 | 5 | 4 |
| 44 | 10 | 5 | 5 | 5 | 4 |
| 46 | 10 | 5 | 5 | 5 | 5 |
| 47 | 10 | 5 | 5 | 5 | 5 |
| 48 | 10 | 5 | 5 | 5 | 5 |
| 49 | 10 | 5 | 5 | 5 | 4 |
| 50 | 10 | 5 | 5 | 5 | 5 |
| 51 | 10 | 5 | 5 | 5 | 5 |
| 52 | 10 | 5 | 5 | 5 | 5 |
| 53 | 10 | 5 | 5 | 5 | 5 |
| 54 | 10 | 5 | 5 | 5 | 5 |
| 55 | 10 | 5 | 5 | 5 | 5 |
| 56 | 10 | 5 | 5 | 5 | 5 |
| 57 | 10 | 5 | 5 | 5 | 5 |
| 59 | 10 | 5 | 5 | 5 | 5 |
| 62 | 10 | 5 | 5 | 5 | 4 |

Test Weeds:
A: *Echinochloa oryzicola*
B: *Monochoria vaginalis*
C: *Rotala indica*
D: *Scirpus juncoides*

Test Example 2 (Pre-emergence Application):

Volcanic ash soil from a field was put in a resin-made pot having an area of 200 cm². After fertilization, soil previously mixed uniformly with the seeds of *Digitaria ciliaris, Setaria viridis, Chenopodium album* or *Polygonum lapathifolium* was scattered on the soil in the pot. The wettable powder prepared in Formulation Example 1 was diluted with water, and a prescribed amount of the diluted preparation was sprayed uniformly to the surface of the soil by means of a small-sized power pressure spray to give 10 g of the active ingredient per are (100 m²).

Cultivation was continued in a greenhouse, and the herbicidal effect was examined on the 28th day from the soil treatment. The results obtained are shown in Table 4 below (the compound numbers in Table 4 correspond to those in Table 1). The herbicidal effect was evaluated based on the same criteria as in Test Example 1.

TABLE 4

| Test Compound | Amount (g/ha) | Herbicidal Effect | | | |
|---|---|---|---|---|---|
| | | E | F | G | H |
| 3 | 10 | 5 | 4 | 5 | 4 |
| 6 | 10 | 4 | 4 | 5 | 4 |
| 7 | 10 | 5 | 5 | 5 | 5 |
| 10 | 10 | 4 | 4 | 5 | 4 |
| 11 | 10 | 5 | 5 | 5 | 5 |
| 12 | 10 | 5 | 5 | 5 | 5 |
| 13 | 10 | 4 | 4 | 5 | 4 |
| 14 | 10 | 5 | 5 | 5 | 5 |
| 16 | 10 | 5 | 5 | 5 | 5 |
| 17 | 10 | 4 | 4 | 5 | 5 |
| 18 | 10 | 5 | 4 | 5 | 5 |
| 19 | 10 | 4 | 4 | 5 | 4 |
| 20 | 10 | 4 | 4 | 5 | 4 |
| 21 | 10 | 4 | 4 | 5 | 4 |
| 22 | 10 | 4 | 4 | 4 | 4 |
| 23 | 10 | 4 | 4 | 4 | 4 |
| 24 | 10 | 4 | 4 | 5 | 5 |
| 26 | 10 | 5 | 5 | 5 | 5 |
| 27 | 10 | 5 | 5 | 5 | 5 |
| 30 | 10 | 5 | 5 | 5 | 5 |
| 31 | 10 | 5 | 5 | 5 | 5 |
| 32 | 10 | 5 | 5 | 5 | 5 |
| 33 | 10 | 5 | 5 | 5 | 5 |
| 34 | 10 | 5 | 5 | 5 | 5 |
| 35 | 10 | 5 | 4 | 5 | 4 |
| 36 | 10 | 5 | 5 | 5 | 5 |
| 37 | 10 | 4 | 4 | 5 | 4 |
| 41 | 10 | 5 | 5 | 5 | 5 |
| 42 | 10 | 5 | 4 | 5 | 5 |
| 44 | 10 | 4 | 4 | 5 | 5 |
| 51 | 10 | 5 | 5 | 5 | 5 |
| 52 | 10 | 5 | 5 | 5 | 5 |
| 53 | 10 | 4 | 4 | 5 | 4 |
| 54 | 10 | 5 | 5 | 5 | 5 |
| 55 | 10 | 5 | 5 | 5 | 5 |
| 56 | 10 | 5 | 5 | 5 | 4 |
| 57 | 10 | 5 | 5 | 5 | 5 |

Test Weeds:
E: *Digitaria ciliaris*
F: *Setaria viridis*
G: *Chenopodium album*
H: *Polygonum lapathifolium*

Test Example 3 (Post-emergence Application):

Volcanic ash soil from a field was put in a resin-made pot having an area of 200 cm². After fertilization, the seeds of *Brassica juncea, Ipomoea purpurea, Echinochloa crusgalli* or *Alopecurus aequalis* were cast on the soil and covered with the soil uniformly. Cultivation was continued in a greenhouse, and when the weeds reached to the 1 to 2-leaf stage, a prescribed amount of the wettable powder prepared in Formulation Example 1 as diluted with water was sprayed to the weeds by means of a small-sized power pressure spray to give 10 g of the active ingredient per are (100 m²). The herbicidal effect was examined on the 21st day from the foliar spray treatment. The results obtained are shown in Table 5 below (the compound numbers in Table 5 are in accordance with those in Table 1). The herbicidal effect was evaluated based on the same criteria as in Test Example 1.

TABLE 5

| Test Compound | Amount (g/ha) | Herbicidal Effect | | | |
|---|---|---|---|---|---|
| | | I | J | K | L |
| 1 | 10 | 4 | 3 | 5 | 5 |
| 3 | 10 | 5 | 4 | 5 | 5 |
| 4 | 10 | 5 | 4 | 5 | 5 |

TABLE 5-continued

| Test Compound | Amount (g/ha) | Herbicidal Effect | | | |
|---|---|---|---|---|---|
| | | I | J | K | L |
| 5 | 10 | 5 | 4 | 5 | 5 |
| 6 | 10 | 5 | 5 | 5 | 5 |
| 7 | 10 | 5 | 5 | 5 | 5 |
| 8 | 10 | 5 | 4 | 5 | 5 |
| 9 | 10 | 5 | 4 | 5 | 5 |
| 10 | 10 | 5 | 5 | 5 | 5 |
| 11 | 10 | 5 | 5 | 5 | 5 |
| 12 | 10 | 5 | 5 | 5 | 5 |
| 13 | 10 | 5 | 4 | 5 | 5 |
| 14 | 10 | 5 | 5 | 5 | 5 |
| 15 | 10 | 5 | 5 | 5 | 5 |
| 16 | 10 | 5 | 5 | 5 | 5 |
| 17 | 10 | 5 | 5 | 5 | 5 |
| 18 | 10 | 5 | 4 | 5 | 5 |
| 19 | 10 | 5 | 5 | 5 | 5 |
| 20 | 10 | 5 | 5 | 5 | 5 |
| 21 | 10 | 5 | 4 | 5 | 5 |
| 22 | 10 | 5 | 5 | 5 | 5 |
| 23 | 10 | 5 | 5 | 5 | 5 |
| 24 | 10 | 5 | 5 | 5 | 5 |
| 25 | 10 | 5 | 5 | 5 | 5 |
| 26 | 10 | 5 | 5 | 5 | 5 |
| 27 | 10 | 5 | 5 | 5 | 5 |
| 28 | 10 | 5 | 5 | 5 | 5 |
| 29 | 10 | 5 | 5 | 5 | 5 |
| 30 | 10 | 5 | 5 | 5 | 5 |
| 31 | 10 | 5 | 5 | 5 | 5 |
| 32 | 10 | 5 | 5 | 5 | 5 |
| 33 | 10 | 5 | 5 | 5 | 5 |
| 34 | 10 | 5 | 5 | 5 | 5 |
| 35 | 10 | 5 | 5 | 5 | 5 |
| 36 | 10 | 5 | 5 | 5 | 5 |
| 37 | 10 | 5 | 5 | 5 | 5 |
| 38 | 10 | 5 | 5 | 5 | 5 |
| 39 | 10 | 5 | 4 | 5 | 5 |
| 40 | 10 | 5 | 5 | 5 | 5 |
| 41 | 10 | 5 | 5 | 5 | 5 |
| 42 | 10 | 5 | 5 | 5 | 5 |
| 43 | 10 | 5 | 4 | 5 | 5 |
| 44 | 10 | 5 | 5 | 5 | 5 |
| 46 | 10 | 5 | 5 | 5 | 5 |
| 47 | 10 | 5 | 4 | 5 | 5 |
| 48 | 10 | 5 | 4 | 5 | 5 |
| 49 | 10 | 5 | 3 | 5 | 5 |
| 50 | 10 | 4 | 3 | 5 | 5 |
| 51 | 10 | 5 | 3 | 5 | 5 |
| 52 | 10 | 5 | 3 | 5 | 5 |
| 53 | 10 | 4 | 4 | 5 | 5 |
| 54 | 10 | 3 | 3 | 5 | 5 |
| 55 | 10 | 3 | 3 | 5 | 5 |
| 56 | 10 | 3 | 3 | 5 | 5 |
| 57 | 10 | 4 | 4 | 5 | 5 |
| 58 | 10 | 4 | 4 | 5 | 5 |
| 59 | 10 | 3 | 3 | 5 | 5 |
| 60 | 10 | 5 | 4 | 5 | 5 |
| 61 | 10 | 3 | 3 | 5 | 5 |

Test Weeds:
I: *Echinochloa crus-galli*
J: *Alopecurus aequalis*
K: *Brassica juncea*
L: *Ipomoea purpurea*

Test Example 4 (Post-emergence Application):

Volcanic ash soil from a field was put in a resin-made pot having an area of 600 cm$^2$. After fertilization, the seeds each of the weeds and the crops shown in Table 6 below were cast on the soil and covered with the soil uniformly. Cultivation was continued in a greenhouse, and when the plants reached to the 2 to 4-leaf stage, a prescribed amount of the emulsifiable concentrate prepared in Formulation Example 2 (active ingredient: Compound No. 18) as diluted with water was sprayed to the plants by means of a small-sized power pressure spray so as to apply the active ingredient in an amount shown in Table 6. For comparison, the compound described in EP-A-288789 (Comparative Compound A) shown below was used. The herbicidal effect and harm to the crops were examined on the 21st day from the foliar spray treatment. The results obtained are shown in Table 6 below (the compound numbers in Table 6 are in accordance with those in Table 1). The herbicidal effect and harm to the crops were evaluated in terms of herbicidal index based on Y(%) obtained from equation:

Y=[1—(Weight of the plants above the ground in a treated pot)/(Weight of the plants above the ground in a non-treated pot)]×100

| Herbicidal Index | Y (%) |
|---|---|
| 0 | 0 to 5 |
| 1 | 6 to 30 |
| 2 | 31 to 50 |
| 3 | 51 to 70 |
| 4 | 71 to 90 |
| 5 | 91 to 100 |

TABLE 6

| Test Compound | Amount (g/ha) | Herbicidal Effect | | | | | | | | | Harm to Crops | |
|---|---|---|---|---|---|---|---|---|---|---|---|---|
| | | M | N | O | P | Q | R | S | T | U | V | W | X |
| 18 | 64 | 5 | 5 | 3 | 5 | 5 | 5 | 5 | 5 | 5 | 5 | 1 | 2 |
| | 32 | 5 | 4 | 2 | 5 | 5 | 5 | 5 | 5 | 5 | 5 | 1 | 2 |
| | 16 | 4 | 4 | 2 | 5 | 5 | 5 | 5 | 5 | 5 | 5 | 0 | 1 |
| | 8 | 3 | 3 | 2 | 5 | 5 | 5 | 5 | 5 | 5 | 5 | 0 | 1 |
| | 4 | 3 | 2 | 1 | 5 | 5 | 5 | 5 | 5 | 4 | 5 | 0 | 0 |
| Comparative Compound A | 64 | 3 | 3 | 2 | 5 | 5 | 5 | 5 | 5 | 5 | 4 | 1 | 2 |
| | 32 | 2 | 2 | 1 | 4 | 4 | 5 | 4 | 4 | 4 | 4 | 1 | 2 |
| | 16 | 1 | 1 | 1 | 4 | 4 | 5 | 4 | 4 | 4 | 4 | 0 | 1 |
| | 8 | 1 | 1 | 0 | 4 | 4 | 4 | 4 | 4 | 4 | 4 | 0 | 0 |
| | 4 | 1 | 1 | 0 | 4 | 3 | 4 | 4 | 3 | 4 | 3 | 0 | 0 |

TABLE 6-continued

| Test Comp- pound | Amount (g/ha) | Herbicidal Effect | | | | | | | | | Harm to Crops | |
|---|---|---|---|---|---|---|---|---|---|---|---|---|
| | | M | N | O | P | Q | R | S | T | U | V | W | X |

Test Plants:
M: *Echinochloa crus-galli*
N: *Setaria viridis*
O: *Alopecurus aequalis*
P: *Polygonum lapathifolium*
Q: *Xanthium strumarium*
R: *Abutilon theophrasti*
S: *Ipomoea purpurea*
T: *Brassica juncea*
U: *Galium spurium*
V: *Viola mandshurica*
W: Corn
X: Wheat Comparative Compound A:

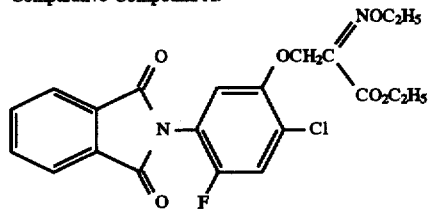

The compounds of the present invention exhibit powerful herbicidal actions while securing sufficient safety to several important crops and are therefore useful as a herbicide.

While the invention has been described in detail and with reference to specific embodiments thereof, it will be apparent to one skilled in the art that various changes and modifications can be made therein without departing from the spirit and scope thereof.

This application is based on Japanese patent application 8-12577, filed on Jan. 29, 1996, incorporated herein by reference.

What is claimed is:

1. A phthalimide compound represented by formula (I):

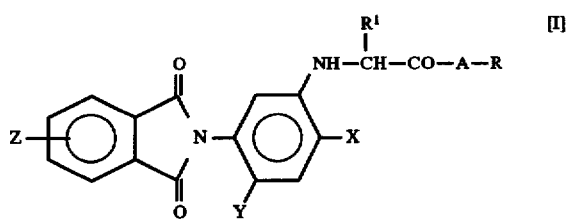

wherein A represents an oxygen atom, a sulfur atom or —$NR^2$—, wherein $R^2$ represents a hydrogen atom or an alkyl group having 1 to 4 carbon atoms, R represents a hydrogen atom; an alkyl group having 1 to 6 carbon atoms; an alkenyl group having 2 to 6 carbon atoms; an alkynyl group having 2 to 6 carbon atoms; a cycloalkyl group having 3 to 6 carbon atoms; a haloalkyl group having 1 to 4 carbon atoms; a cyanoalkyl group having 2 to 5 carbon atoms; an alkoxyalkyl group having 2 to 6 carbon atoms; an alkylthioalkyl group having 2 to 6 carbon atoms; an alkylsulfonylalkyl group having 2 to 6 carbon atoms; an acyloxyalkyl group having 3 to 7 carbon atoms; an alkoxycarbonylalkyl group having 3 to 8 carbon atoms; a phenyl group; an alkyl group having 1 to 3 carbon atoms which is substituted with a phenyl group; a 3- to 6-membered heterocyclic group containing one or two hetero atoms selected from an oxygen atom, a sulfur atom, and a nitrogen atom; or an alkyl group having 1 to 3 carbon atoms which is substituted with a 3- to 6-membered heterocyclic group containing one or two hetero atoms selected from an oxygen atom, a sulfur atom, and a nitrogen atom, when A represents —$NR^2$—, R may be taken together with A to form a 5- or 6-membered heterocyclic group containing one or two nitrogen atoms and zero or one oxygen atom (the heterocyclic group may be substituted with one or two methyl groups), $R^1$ represents a hydrogen atom or an alkyl group having 1 to 4 carbon atoms, X represents a halogen atom, Y represents a hydrogen atom or a halogen atom, Z represents a hydrogen atom, an alkyl group having 1 to 3 carbon atoms, or a halogen atom, and when R represents a phenyl group; an alkyl group having 1 to 3 carbon atoms which is substituted with a phenyl group; a 3- to 6-membered heterocyclic group containing one or two hetero atoms selected from an oxygen atom, a sulfur atom, and a nitrogen atom; or an alkyl group having 1 to 3 carbon atoms which is substituted with a 3- to 6-membered heterocyclic group containing one or two hetero atoms selected from an oxygen atom, a sulfur atom, and a nitrogen atom, the phenyl group or the heterocyclic group may be substituted with one to three groups, which may be the same or different and selected from a halogen atom, an alkyl group having 1 to 4 carbon atoms, a trifluoromethyl group, an alkoxy group having 1 to 4 carbon atoms, an acyloxy group having 2 to 5 carbon atoms, an alkylthio group having 1 to 4 carbon atoms, an alkylsulfonyl group having 1 to 4 carbon atoms, a nitro group, a cyano group, and an alkoxycarbonyl group having 2 to 5 carbon atoms.

2. A phthalimide compound according to claim 1, wherein A is an oxygen atom or —$NR^2$—, wherein $R^2$ represents a hydrogen atom or an alkyl group having 1 to 4 carbon atoms.

3. A phthalimide compound according to claim 1, wherein A is an oxygen atom.

4. A phthalimide compound according to claim 1, wherein R represents a hydrogen atom; an alkyl group having 1 to 6 carbon atoms; an alkenyl group having 2 to 6 carbon atoms; an alkynyl group having 2 to 6 carbon atoms; a cycloalkyl group having 3 to 6 carbon atoms; a haloalkyl group having 1 to 4 carbon atoms; a cyanoalkyl group having 2 to 5 carbon atoms; an alkoxyalkyl group having 2 to 6 carbon atoms; an acyloxyalkyl group having 3 to 7 carbon atoms; an alkoxycarbonylalkyl group having 3 to 8 carbon atoms; a phenyl group; an alkyl group having 1 to 3 carbon atoms which is substituted with a phenyl group; a tetrahydrofuryl group which is substituted with an acyloxy group having 2 to 5 carbon atoms; or a tetrahydropyran-2-ylmethyl group; or when A represents $-NR^2-$, R is taken together with A to form a piperidino group.

5. A phthalimide compound according to claim 1, wherein R is a hydrogen atom; an alkyl group having 1 to 6 carbon atoms; an alkenyl group having 2 to 6 carbon atoms; an alkynyl group having 2 to 6 carbon atoms; a cycloalkyl group having 3 to 6 carbon atoms; a haloalkyl group having 1 to 4 carbon atoms; a cyanoalkyl group having 2 to 5 carbon atoms; an alkoxyalkyl group having 2 to 6 carbon atoms; an acyloxyalkyl group having 3 to 7 carbon atoms; an alkoxycarbonylalkyl group having 3 to 8 carbon atoms; an alkyl group having 1 to 3 carbon atoms which is substituted with a phenyl group; a tetrahydrofuryl group which is substituted with an acyloxy group having 2 to 5 carbon atoms; or a tetrahydropyran-2-ylmethyl group.

6. A phthalimide compound according to claim 1, wherein $R^1$ is a hydrogen atom or an alkyl group having 1 to 3 carbon atoms.

7. A phthalimide derivative according to claim 1, wherein X is a chlorine atom or a bromine atom.

8. A phthalimide compound according to claim 1, wherein Y is a hydrogen atom, a fluorine atom or a chlorine atom.

9. A phthalimide compound according to claim 1, wherein Z is a hydrogen atom, a methyl group or a halogen atom.

10. A phthalimide compound according to claim 2, wherein Z is a hydrogen atom, a fluorine atom bonded at the 4-position, or a chlorine atom bonded at the 4-position.

11. A phthalimide compound according to claim 1, wherein A represents an oxygen atom or $-NR^2-$, wherein $R^2$ represents a hydrogen atom or an alkyl group having 1 to 4 carbon atoms, R represents a hydrogen atom; an alkyl group having 1 to 6 carbon atoms; an alkenyl group having 2 to 6 carbon atoms; an alkynyl group having 2 to 6 carbon atoms; a cycloalkyl group having 3 to 6 carbon atoms; a haloalkyl group having 1 to 4 carbon atoms; a cyanoalkyl group having 2 to 5 carbon atoms; an alkoxyalkyl group having 2 to 6 carbon atoms; an acyloxyalkyl group having 3 to 7 carbon atoms; an alkoxycarbonylalkyl group having 3 to 8 carbon atoms; a phenyl group; an alkyl group having 1 to 3 carbon atoms which is substituted with a phenyl group; a tetrahydrofuryl group substituted with an acyloxy group having 2 to 5 carbon atoms; or a tetrahydropyran-2-ylmethyl group; or when A represents $-NR^2-$, R is taken together with A to form a piperidino group, and Z represents a hydrogen atom, a methyl group or a halogen atom.

12. A phthalimide compound according to claim 11, wherein $R^1$ represents a hydrogen atom or an alkyl group having 1 to 3 carbon atoms, X represents a chlorine atom or a bromine atom, Y represents a hydrogen atom, a fluorine atom or a chlorine atom; and Z represents a hydrogen atom, a fluorine atom bonded at the 4-position or a chlorine atom bonded at the 4-position.

13. A phthalimide compound according to claim 12, wherein A represents an oxygen atom, and R represents a hydrogen atom; an alkyl group having 1 to 6 carbon atoms; an alkenyl group having 2 to 6 carbon atoms; an alkynyl group having 2 to 6 carbon atoms; a cycloalkyl group having 3 to 6 carbon atoms; a haloalkyl group having 1 to 4 carbon atoms; a cyanoalkyl group having 2 to 5 carbon atoms; an alkoxyalkyl group having 2 to 6 carbon atoms; an acyloxyalkyl group having 3 to 7 carbon atoms; an alkoxycarbonylalkyl group having 3 to 8 carbon atoms; an alkyl group having 1 to 3 carbon atoms which is substituted with a phenyl group, a tetrahydrofuryl group substituted with an acyloxy group having 2 to 5 carbon atoms, or a tetrahydropyran-2-ylmethyl group.

14. A herbicide composition which comprises as an active ingredient a phthalimide compound according to any one of claims 1 to 13.

* * * * *